US005922583A

United States Patent [19]
Morsey

[11] Patent Number: 5,922,583
[45] Date of Patent: Jul. 13, 1999

[54] METHODS FOR PRODUCTION OF RECOMBINANT PLASMIDS

[75] Inventor: Mohamad A. Morsey, Saskatoon, Canada

[73] Assignee: Biostar Inc., Saskatchewan, Canada

[21] Appl. No.: 08/732,612

[22] Filed: Oct. 16, 1996

Related U.S. Application Data

[63] Continuation-in-part of application No. 08/564,973, Nov. 30, 1995., which is a continuation-in-part of application No. 08/548,059, Oct. 17, 1995.

[51] Int. Cl.$^6$ .............................. C12N 15/00; C12N 1/20; C12N 5/00; C07H 21/04
[52] U.S. Cl. ................... 435/172.3; 435/69.1; 435/91.1; 435/91.4; 435/183; 435/252.3; 435/252.33; 435/320.1; 435/325; 536/23.1; 536/23.7
[58] Field of Search .......................... 435/6, 320.1, 325, 435/420, 243, 252.3, 91.1; 536/23.1; 514/44

[56] References Cited

U.S. PATENT DOCUMENTS

| | | |
|---|---|---|
| 4,190,495 | 2/1980 | Curtiss, III . |
| 4,550,081 | 10/1985 | Stocker . |
| 4,735,801 | 4/1988 | Stocker . |
| 4,760,022 | 7/1988 | Molin et al. ............................ 435/320 |
| 4,837,151 | 6/1989 | Stocker . |
| 4,888,170 | 12/1989 | Curtiss, III . |
| 4,920,048 | 4/1990 | Diderichsen . |
| 4,968,619 | 11/1990 | Curtiss, III . |
| 5,077,044 | 12/1991 | Stocker . |
| 5,210,035 | 5/1993 | Stocker . |
| 5,294,441 | 3/1994 | Curtiss, III . |
| 5,387,744 | 2/1995 | Curtiss, III et al. . |
| 5,399,346 | 3/1995 | Anderson et al. . |
| 5,702,916 | 12/1997 | Molin et al. ............................ 435/69.1 |

FOREIGN PATENT DOCUMENTS

| | | |
|---|---|---|
| 2177097 | 1/1987 | United Kingdom . |
| WO 88/09669 | 12/1988 | WIPO . |
| WO 89/03427 | 4/1989 | WIPO . |
| WO 90/02484 | 3/1990 | WIPO . |
| WO 90/11687 | 10/1990 | WIPO . |
| WO 90/11688 | 10/1990 | WIPO . |
| WO 90/12086 | 10/1990 | WIPO . |
| WO 91/06317 | 5/1991 | WIPO . |
| WO 92/09684 | 6/1992 | WIPO . |
| WO 94/24291 | 10/1994 | WIPO . |

OTHER PUBLICATIONS

Saqib et al., The expression of Escherichia coli diaminopimelate decaboxylase in mouse 3T3 cells, Biochim. Biophys. Acta., vol. 1219, pp. 398–404, 1994.
Duncan et al., Purification and characterization of the D–alanyl–D–alanine–adding enzyme from *escherichia coli*, Biochemistry, vol. 29, pp. 2379–2386, 1990.
Mulligan, The basic science of gene therapy, Science, vol. 260, pp. 926–932, May 1993.
Orkin et al., Report and recommendations of the panel to assess the NIH investment in research on gene therapy, pp. 1–41, Dec. 1995.

Cichutek, K. "Nucleic Acid Immunization: A Prophylactic Gene Therapy?", *Vaccine*, 12:1520–1525.
Curtiss III, R, et al., "Stabilization of Recombinant Avirulent Vaccine Strains In Vivo," *Res. Mircobiol.* 141:797–805 (1990).
Diderichsen, B. "A Genetic System for Stabilization of Cloned Genes in *Bacillus Subtilis*", pp. 35–46 (1986).
Donnelly, J.J. et al., "Immunization with Polynucleotides: A Novel Approach to Vaccination" *The Immunologist*, 2: 20–26 (1994).
Donnenberg, M.S. et al., "Construction of an eae Deletion Mutant of Enteropathogenic *Escherichia coli* by Using a Positive–Selection Suicide Vector" *American Society for Microbiology*, 59:4310–4317 (1991).
Dwivedi, C.P. et al., "Instability of Plasmid–Harboring Strain of *E. coli* in Continuous Culture" *Biotechnology and Bioengineering*, 24:1465–1468 (1982).
Ferrari, E. et al., "Isolation of an Alanine Racemase Gene from *Bacillus Subtilis* and Its Use for Plasmid Maintenance in B. Subtilis" *Biotechnology*, 3:1003–1007 (1985).
Galan, J.E. et al., "Cloning and Characterization of the asd gene of Salmonella Typhimurium: Use in Stable Maintenance of Recombinant Plasmids in Salmonella Vaccine Strains" *Gene*, 94:29–35 (1990).
Gerdes, K "The Parb (HOK/SOK) Locus of Plasmid R1: A General Purpose Plasmid Stabilization System," *Biotechnology*, 6:1402–1405 (1988).
Gerdes, K. et al., "Unique Type of Plasmid Maintenance Function: Postsegregational Killing of Plasmid–free Cells" *Proc. Natl. Acad. Sci. USA*, 83:3116–3120 (1986).
Hodgson, C.P. "The Vector Void in Gene Therapy" *Biotechnology*, 13:222–225 (1995).
Imanaka, T. et al., "Phenotypic Stability of trp Operon Recombinant Plasmids in *Escherichia coli*" *J. Gen. Microbiol*, 118:253–261 (1980).

(List continued on next page.)

*Primary Examiner*—George C. Elliott
*Assistant Examiner*—Andrew Wang
*Attorney, Agent, or Firm*—Morrison & Foerster, LLP

[57] ABSTRACT

The invention relates to a culture system for stable and high-level production of DNA contained on recombinant plasmids, and to the bacteria and plasmids which comprise the culture system. The bacterial cell chromosome is irreversibly altered, in one embodiment, so as to produce a substance toxic to the bacterium; in a second embodiment so as to render the cells unable to synthesize and assimilate an essential metabolite, and, in a third embodiment, to be incapable of producing a required intracellular protein that does not lead to a secreted product. In every case, the recombinant plasmid includes genetic material which functionally complements the chromosomal alteration. If the DNA on the plasmid is to be used in therapeutic applications or for administration to eukaryotes, the genetic material will have no functional or structural equivalent in eukaryotic cells, and will not result in production of mRNA or a polypeptide that acts on any eukaryotic cell component. Any peptide produced is, desirably, not toxic to the bacterial cells.

21 Claims, 11 Drawing Sheets

OTHER PUBLICATIONS

Jensen, R. B. et al., "Programmed Cell Death in Bacteria: Proteic Plasmid Stabilization Systems", *Mol. Microbiology,* 17:205–210 (1995).

Khan, M. et al., "Plasmid Cloning Vehicles Derived from Plasmids ColE1, F, R6K, and RK2" *Methods in Enzymology,* 68:268–280 (1979).

Lugtenberg, E.J. J. et al., "Temperature–Sensitive Mutants of *Escherichia coli* K–12 with Low Activities of the L–Alanine Adding enzyme and the D–Alanyl–D–Alanine Adding Enzyme" *J. Bacteriology,* 110:35–40 (1972).

Miller, J. "A Short Course in Bacterial Genetics" *CSH Laboratory Press* (1992).

Nakayama, K. et al., "Construction of an ASD+ Expression–Cloning Vector: Stable Maintenance and High Level Expression of Cloned Genes in a Salmonella Vaccine Strain" *Biotechnology,* 6:693–697 (1988).

Nilsson, J. et al., "Stabilization of *Escherichia coli* Trytophan–Production Vectors in Continuous Cultures: A Comparison of Three Different Systems" *Biotechnology,* 4:901–903 (1986).

Park, J.T. "MicroReview: Why Does *Escherichia coli* Recycle its Cell Wall Peptides?", *Molecular Microbiology,* 17:421–426 (1995).

Porter, R.D. et al., "Use of the *Escherichia coli* SSB Gene to Prevent Bioreactor Takeover by Plasmidless Cells" *Biotechnology,* 8:47–51 (1990).

Rasmussen, P.B. et al., "Genetic Analysis of the parB+ Locus of Plasmid R1" *Mol. Gen. Genet.,* 209:22–128 (1987).

Robertson, J.S. "Safety Considerations for Nucleic Acid Vaccines" *Vaccine,* 12:1526–1528 (1994).

Sambrook et al., "Molecular Cloning" A Laboratory Manual.

Smith, H. "Regulatory Considerations for Nucleic Acid Vaccines" *Vaccine,* 12:1515–1519 (1994).

Steffes, C. et al., "The lysP Gene Encodes the Lysine–Specific Permease" *Journal of Bacteriology* 174:3242–3249 (1992).

Stragier, P. et al., "Regulation of Diaminopimelate Decarboxylase Synthesis in *Escherichia coli*", *J. Mol. Biol.,* 168:307–320 (1983).

Ulmer, J. B. et al., "Polynucleotide Vaccines" *Curr. Opin. Invest. Drugs,* 2:983–989 (1993).

FIG. 11

Molecule Name: Ts mur F gene  1360 bps DNA Linear
Sequence Printed: 1 – 1360 (Full)  Date Printed 08 Oct. 1996
Description: Coding sequence of Ts mur F gene

```
   1  ATGATTAGCG  TAACCCTTAG  CCAACTTACC  GACATTCTCA  ACGGTGAACT  GCAAGGTGCA
  61  GATATCACCC  TTGATGCTGT  AACCACTGAT  ACCCGAAAAC  TGACGAAGGG  CTGCCTGTTT
 121  GTTGCCCTGA  AGGCGAACG   TTTTGATGCC  CACGATTTTG  CCGACCAGGC  GAAAGCTGGC
 181  GCGGCAGGCG  CACTACTGGT  TAGCCGTCCG  CTGGACATCG  ACCTGCCGCA  GTTAATCGTC
 241  AAGGATACGC  GTCTGGCGTT  TGGTGAACTG  GCTGCATGGG  TTCGCCAGCA  AGTTCCGGCG
 301  CGCGTGGTTG  CTCTGACGGG  GTCCTCCGGC  AAAACCTCCG  TTAAAGAGAT  GACGGCGGCG
 361  ATTTTAAGCC  AGTGCGGCAA  CACGCTTTAT  ACGGCAGGCA  CGACATCGGT  TGAACTTGGC
 421  GTACCGATGA  CGCTGTTCCG  CTTAACGCCG  GAATACGATT  ACGCAGTTAT  ACGTGCGCTG
 481  GCGAACCATC  AGGGCGAAAT  AGCCTGGACT  GTGAGTCTGA  CTCGCCCGGA  ACGTGCCGCT
 541  GTCAACAACC  TGGCAGCGGC  GCATCTGGAA  GGTTTTTGGCT  CGCTTGCGGG  TGTCGCGAAA
 601  GCGAAAGGTG  AAATCTTTAG  CGGCCCTGCCG  GAAAACGGTA  GCAAAGTGTG  GAACGCCGAC
 661  AACAACGACT  GGCTGAACTG  GCAGAGCGTA  ATTGGCTCAC  TCGCCCATCA  GCGTTTCTCA
 721  CCCAATGCCG  CCAACAGCGA  TTTCACCGCC  ACCAATATCC  ATGTGACCTC  GCACGGTACG
 781  GAATTTACCC  TACAAACCCC  AACCGGTAGC  GTCGATGTTC  TGTCCGTT    GCCGGGCGT
 841  CACAATATTG  CGAATGCGCT  GACAGCCCGCT  GCGCTCTCCA  TGTCCGTGGG  CGCAACGCTT
 901  GATGCTATCA  AGCGGGGCT   GGCAAATCTG  AAAGCTGTTC  CAGGCCGTCT  GTTCCCCATC
 961  CAACTGGCAG  AAAACCAGTT  GCTGCTCGAC  GACTCCTACA  ACCCCAATGT  CGGTTCAATG
1021  ACTGCAGCAG  TCCAGGTACT  GGCTGAAATG  CCCGGCTACC  GCGTGCTGGT  GGTGGGCGAT
1081  ATGGCGGAAC  TGGGCGCTGA  AAGCGAAGCC  TGCAAACAAA  AGGTGGGCGA  GCGGGCAAAA
1141  GCTGCTGGTA  TTGACCGCGT  GTAAGCGTG   GGTAAACAAA  GCCATGCTAT  CAGCACCCGC
1201  CAGCGGCGTT  GGCGAACATT  TGCTGATAA   AACTGCGTTA  ATTACGCGTC  TTAAATTACT
1261  GATTGCTGAG  CAACAGTAA   TTACGATTT   AGTTAAGGGT  TCACGTAGTG  CCGCCATGGA
1321  AGAGGTAGTA  CGCGCTTTAC  AGGAGAATGG  GACATGTTAG
```

METHODS FOR PRODUCTION OF RECOMBINANT PLASMIDS

This application is a continuation-in-part of U.S. Ser. No. 08/564,973 filed Nov. 30, 1995 which is continuation-in-part of U.S. Ser. No. 08/548,059 filed Oct. 17, 1995, the contents of which are incorporated herein by reference.

BACKGROUND OF THE INVENTION

The combination of genetically engineered bacterial cells and recombinant plasmids are the foundation of industrial biotechnology. For example, they are used for production of industrially and medically important proteins such as enzymes, cytokines, growth hormones, and antigens or as live bacterial vaccines. The advent of DNA immunization and gene therapy technologies has added another dimension to the use of genetically engineered bacterial cells and their companion recombinant plasmids. For the purpose of these technologies, expression of proteins in genetically engineered bacterial cells is no longer the principal objective, which is, instead, the replication and high-level production of structurally and genetically stable recombinant plasmids carrying foreign DNA. This is because the DNA, rather than a protein encoded therein, is the desired product for use in DNA immunization or gene therapy.

Consequently, the present invention relates to the use of genetically-engineered bacterial cells and their companion recombinant plasmids for cloning of foreign DNA. More particularly, the invention provides a method whereby foreign DNA suitable for use in DNA immunization and gene therapy can be replicated and produced in large quantities in these companion recombinant plasmids.

Early on during the development of recombinant DNA technology, it was realized that a major challenge to that emerging technology was the stable maintenance of recombinant plasmids in bacterial cells. It was also realized that this problem stems largely from the heavy metabolic burden imposed on genetically-engineered bacterial cells as a result of high-level expression of proteins which are of no value to them.

Consequently, when propagating genetically-engineered bacterial cells that have no incentive to maintain the recombinant plasmid, over time, plasmid-free bacterial cells appear at increasing frequency. Because of the heavier metabolic burden on plasmid-harbouring bacterial cells, plasmid-free bacterial cells have higher growth rates. Accordingly, within a relatively short period of time, the bacterial culture can become dominated by plasmid-free bacterial cells, thus leading to a decreasing plasmid yield.

Since plasmid-harbouring bacterial cells are almost always at a growth disadvantage as compared to plasmid-free bacterial cells, any plasmid-free bacterial cells which arise during extended culture periods will eventually take over the fermentation bioreactor. In this regard, it is estimated that a 10% growth advantage for plasmid-free bacterial cells will result in bioreactor take-over within 150 hours of culture at a dilution rate of 1 hr/L even if the plasmid loss frequency is only $1 \times 10^{-7}$. These calculations underscore the need for a plasmid stabilization system that is 100% effective in preventing plasmid loss since it is not uncommon that bacterial cells are grown for 300 hours of continuous culture within industrial bioreactors.

These observations indicate that absence of selective pressure for maintaining recombinant plasmids in propagated genetically engineered bacterial cells results in a decreasing frequency of plasmid-harbouring bacterial cells, and that plasmid loss is further accentuated by the slower growth rate of plasmid-harbouring bacterial cells.

Several methods have been devised to enhance recombinant plasmid stability in bacterial cell populations. All these methods have a common underlying principle: the application of selective pressure to ensure the growth and multiplication of only those bacterial cells that are harbouring the recombinant plasmid.

In one of these methods, selective pressure is applied to bacterial cells by cloning the desired gene on a recombinant plasmid that also carries one or more genes specifying resistance to specific antibiotics. Thus, addition of the specific antibiotic(s) to a culture of growing bacterial cells ensures that only the ones harbouring the recombinant plasmid survive.

Although antibiotic resistance genes have been very useful and effective in providing a means of recombinant plasmid stability, their use has serious drawbacks. Firstly, addition of antibiotics in the culture medium during fermentation on an industrial scale is expensive. Secondly, in those cases where the mechanism of antibiotic resistance is based on secretion of an antibiotic-inactivating compound, some plasmid-free bacterial cells may survive because surrounding plasmid-harbouring bacterial cells secrete enough of the antibiotic-inactivating compound into the culture medium so as to permit survival of both plasmid-harbouring and plasmid-free bacterial cells. Thirdly, the use for DNA immunization and gene therapy of recombinant plasmid DNA containing antibiotic resistance genes is viewed unfavourably because such genes might be incorporated into the animal genome, or into the genome of endogenous microflora. Fourthly, residual antibiotics that contaminate plasmid DNA (as a result of their addition to the culture medium) could provoke sensitivity and/or systemic allergic reactions in certain animals treated with such plasmid DNA.

As an alternative to the use of antibiotic resistance genes, several methods have been devised to enhance recombinant plasmid stability and prevent accumulation of plasmid-free bacterial cells. The common thread to these methods is to make the survival of genetically-engineered bacterial cells dependent on a functional complementation system using a plasmid-borne gene.

These known methods can be divided into three groups depending on the type of polypeptide encoded by the gene used. However, each of the known methods is either impractical in reducing the rate at which plasmid-free bacterial cells arise under industrial conditions and/or unsuitable for production of recombinant plasmids for use in eukaryotes, such as for DNA immunization and gene therapy. Each group of methods will be described in turn.

The first group comprises methods in which a chromosomal defect results in the failure to produce an essential nutrient and the plasmid-borne gene encodes an enzyme essential for the biosynthesis of this nutrient (e.g. an amino acid) that normally exists in commonly used bacterial growth medium (Dwivedi, C. P. et al. *Biotechnology and Bioengineering* (1982) 24: 1465–1668; Imanaka, T. et al. *J Gen Microbiol* (1980) 118: 253–261). These methods as set forth in the prior art require that the plasmid-harbouring bacterial cells be grown on special and expensive synthetic medium lacking the amino acid in question. This is impractical in industrial bioreactor conditions.

The second group comprises methods wherein a chromosomal defect resides in defective production of an end-product that is required, and the plasmid-borne gene encodes an enzyme that synthesizes this end-product, but where the end-product does not exist in commonly used bacterial growth medium (Diderichsen, B. *Bacillus Molecular Genetics and Biotechnology Applications* (1986) pp. 35–46; Ferrari, E. et al. *BioTechnology* (1985) 3: 1003–1007; Galan, J. E. et al. *Gene* (1990) 94: 29; Nakayama, K. et al. *BioTechnology* (1988) 6: 696; Curtiss, R. et al. *Res Microbiol* (1990) 141: 797).

To date, this method has focused on synthesis of amino acids that are incorporated into the bacterial cell wall. The utility of this approach in DNA immunization and gene therapy is hampered for the following reasons.

The enzymes that have been used in these situations to date (e.g., aspartate semialdehyde dehydrogenase (asd) or alanine racemase (alr)) catalyse the formation of a small diffusible growth factor (aspartate semialdehyde and D-alanine, respectively), and the factor may accumulate in the culture medium under industrial bioreactor conditions. Such accumulation contributes to plasmid loss because of a cross-feeding effect in which plasmid-harbouring bacterial cells (producing the small diffusible growth factor) support the growth of plasmid-free bacterial cells. Therefore, to avoid such cross-feeding effects, this type of gene has been used with low-copy-number plasmids, i.e., of a type which occur as only 1 or 2 copies per bacterial cell. Clearly using low-copy-number recombinant plasmids is impractical for production of industrial quantities of plasmid DNA, where plasmids of a type resulting in high copy numbers are desired. High-copy-number recombinant plasmids are those of a type which occur somewhere on the order of about 50 to several hundreds of plasmid copies per bacterial cell.

The asd gene as the plasmid-borne gene has another drawback. This drawback is related to the recent findings (Park, J. T. *Molecular Microbiology* (1995) 17: 421–426) that bacterial cells (e.g. *E. coli*) actually degrade approximately 50% of their peptidoglycan layer. The degradation product is a tripeptide consisting of L-alanine/D-glutamate/mesodiaminopimelic acid, which is reused by the bacterial cells to form peptidoglycan thus conserving energy that the bacterial cell would have expended synthesizing new tripeptide components of peptidoglycan. A high proportion of this tripeptide is released into the culture medium and is available to be taken up by neighbouring bacterial cells for incorporation into their own peptidoglycan layer. The asd gene encodes the first enzyme in the biosynthesis of the amino acid mesodiaminopimelic acid (dap) which is already included in this tripeptide. However, since bacterial cells can recycle their own peptidoglycan, and can secrete the tripeptide containing the replaced amino acid dap, there is no selective pressure on the plasmid-harboring bacterial cells to maintain their plasmids.

The third group comprises methods wherein the plasmid-borne gene encodes a protein that has functional and structural counterparts in eukaryotic cells and/or is capable of acting upon a eukaryotic cell component. The use of such genes represents a major safety concern because of the potential for the proteins encoded by these genes to function in eukaryotic cells and because of the potential for integration of the gene itself into the eukaryotic genome by homologous recombination. Examples include genes encoding proteins involved in the vital function of DNA replication (single strand DNA binding protein; Porter, R. D. et al. *BioTechnology* (1990) 8: 47) or a tRNA-related function (valine tRNA synthetase; Nilsson, J. and Skogman, G. *BioTechnology* (1986) 4: 901–903).

The use as a marker of the gene encoding alanine racemase (alr) is also impractical for producing recombinant plasmid DNA for DNA immunization and gene therapy because this enzyme can function in eukaryotic cells. Alanine racemase catalyses the conversion of L-alanine into D-alanine. Since eukaryotic cells contain L-alanine as a natural component of their biochemical make-up, the use of alanine racemase can interfere with the biochemical reactions involved in L-alanine biosynthesis in eukaryotic cells and could lead to the formation of an amino acid (D-alanine) that does not naturally exist in eukaryotic cells.

Recently, a meeting of the World Health Organization (WHO) devoted to issues of DNA immunization and gene therapy was convened (Nucleic Acid Vaccines, WHO, Geneva, as reported in Cichutek, K. *Vaccine* (1994) 12: 1520; Robertson, J. S. *Vaccine* (1994) 12: 1526; Smith, H. *Vaccine* (1994) 12: 1515). At this meeting of experts in the field of DNA immunization and gene therapy, as well as experts from regulatory authorities, a number of matters were declared crucial issues that have to be addressed in order to pave the way for these technologies to produce clinically useful products. These included structural and genetic stability of recombinant plasmids, the potential integration of recombinant plasmid DNA within host chromosomes, as well as the use of marker genes (e.g. antibiotic resistance genes) for selection and propagation of the desired plasmid-harbouring bacterial cells.

Thus, for the purpose of introducing foreign DNA into eukaryotes, such as for DNA immunization and gene therapy, there is a need for a system whereby genetically-engineered bacterial cells can be used for production of plasmid-borne foreign genes without the use of genetic material which itself can integrate within the eukaryotic genome or by virtue of its encoded product can function within eukaryotic cells or act upon any eukaryotic cell component.

In addition, improved methods for stable and high-productivity cloning in bacteria would be helpful simply for production of large quantities of desired DNA.

DISCLOSURE OF THE INVENTION

The invention provides recombinant systems for production of large quantities of desired DNA, and in particular DNA that can be safely introduced into eukaryotes. The systems of the present invention offer advantages of efficiency and safety over art-known methods.

Thus, in one aspect, the invention is directed to culture systems and the components thereof which are designed for stable, high-level production of recombinant plasmids. In these culture systems, bacterial cells are employed wherein the bacterial cell chromosome is irreversibly modified to effect production of a substance toxic to the bacterial cells. The bacterial cells are modified to contain recombinant plasmids wherein the recombinant plasmids include genetic material that effects production of a second substance which neutralizes the toxicity of the first substance that would otherwise be toxic to the cells under the cell culture system conditions. The invention is directed also to the bacterial cells and plasmids useful in this cell culture system, and to methods to produce high levels of desired DNA using these materials. The plasmids employed in this system may further include a foreign DNA operatively linked to control sequences functional only in eukaryotes, whereby the foreign DNA is expressed in eukaryotic cells, but not in prokaryotic cells.

In a second aspect, the invention relates to cell culture systems for the stable, high-level production of recombinant plasmids wherein the bacterial cell chromosome of the bacteria in these cultures is irreversibly modified so as to render the cell incapable of producing an essential metabolite and also incapable of the uptake of the metabolite from the culture medium. The recombinant plasmid used in this system is a plasmid which includes genetic material which restores either the ability to synthesize the metabolite or the ability to take up the metabolite from the medium or both. This aspect of the invention also includes the bacterial cells and plasmids which are components of the cell culture system and methods to produce large quantities of DNA using the system. The plasmids may also be modified to contain a foreign DNA operably linked to control sequences functional only in eukaryotes, so that the foreign DNA is expressed in eukaryotic cells, but not in prokaryotic cells.

In still another aspect, the invention provides a culture system for stable and high-level production of recombinant plasmids for DNA immunization and gene therapy, comprising genetically engineered bacterial cells and recombinant plasmids. In this system, the bacterial cell chromosome is irreversibly altered and the bacterial cells are propagated under conditions such that the viability of the bacterial cells is dependant on the recombinant plasmid. The recombinant plasmid includes genetic material which functionally complements the chromosomal alteration, but the genetic material has no functional or structural equivalent in eukaryotic cells and does not produce any protein capable of acting upon any eukaryotic cell component. The protein encoded by the compensating genetic material, or any product thereof, is also incapable of being secreted by, or produced at levels toxic for, the bacterial cells. The recombinant plasmid is also adapted to include foreign DNA operatively linked to control sequences functional only in eukaryotes so as to effect expression of the foreign DNA only in eukaryotic cells, but not in prokaryotes. The invention is also directed to the bacterial cells and high-copy-number plasmids used in this cell culture system, as well as to methods to stably prepare foreign DNA for administration to eukaryotes using this system.

In still other aspects, the invention is directed to methods to provide a desired foreign DNA to eukaryotic cells or a eukaryotic subject which method comprises contacting said cells or administering to said subject DNA prepared by the methods of the invention, or administering to the subject the bacterial cells containing the desired DNA.

BRIEF DESCRIPTION OF THE DRAWINGS

FIG. 11 (SEQ ID NO: 1) shows the nucleotide sequence of the temperature-sensitive murF gene derived from TKL-46.

MODES OF CARRYING OUT THE INVENTION

Figure 1:
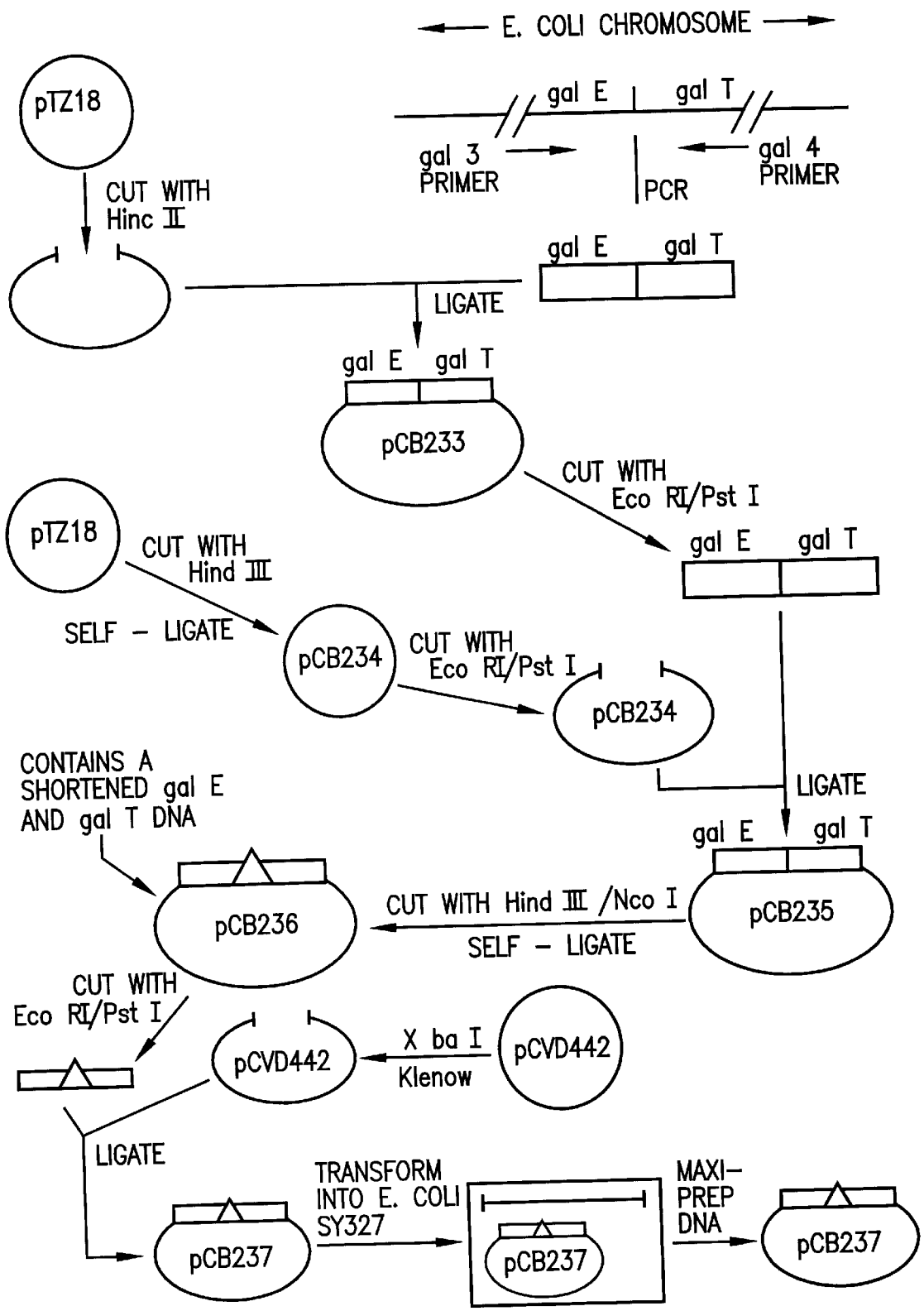
FIG. 1 shows the construction of recombinant plasmid pCB237.

The present invention provides culture systems which permit the stable production of a desired DNA. In some instances, the desired DNA will be a foreign DNA whose expression in a eukaryotic cell is desired either for immunization or genetic therapy. This "expression" includes simple transcription as well as production of polypeptides. Thus, the foreign DNA for use in eukaryotes may be employed in antisense therapy, as well as in genetic therapy involving production of therapeutic proteins or markers.

When the foreign DNA is to be administered to a eukaryote, the amplified replicated DNA may be recovered and administered in the form of a pharmaceutical composition using standard formulation techniques. Suitable formulations for administering DNA include various excipients, for example, liposomes, dendrimers, aquasomes, cochleates, isotonic saline or PBS. The DNA can also be recovered and ligated into a retroviral vector. In addition to the DNA per se, the bacterial cells themselves containing the replicated DNA can be administered to a eukaryotic subject. The cells are chosen or manipulated so as to have the appropriate features which will permit the included DNA to locate in the nucleus of, for example, macrophage, so that expression of the foreign DNA may be effected. Thus, the prokaryotes administered must be able to exit the lysosome, disintegrate, and permit the DNA to enter the nucleus. Some bacterial hosts, such as Shigella and Listeria strains are innately capable of effecting these results. In addition to expressible DNA, vaccines which involve simply "naked DNA" have also been used successfully.

In general, administration of the DNA, either per se in a pharmaceutical composition or contained in the bacterial cells, is by injection; typically, intravenous, intramuscular, intradermal or subcutaneous. Administration may also be intranasal or oral, or by a particle bombardment technique. However, any effective systemic means of administration may be employed.

All of the culture systems of the invention rely on complementation of a destructive feature found in the bacterial chromosome by the effect of genetic material contained on a plasmid which is itself to be stably replicated in the bacterial culture. In one embodiment, the bacterial chromosome produces a substance toxic to the bacterial cells and this substance is counteracted by a substance produced by genetic material on the plasmid. In a second embodiment, the bacterial chromosome is modified so as to render the cell incapable of producing an essential metabolite and also incapable of the uptake of this metabolite from the culture medium, and the recombinant plasmid restores one or both of these abilities. In either of these cases, an additional desired DNA sequence to be amplified may be included in the plasmid; in addition, this desired DNA may be operably linked to control sequences for expression exclusively in eukaryotic cells.

In a third approach, in this case for production of a foreign DNA operably linked to control sequences which effect expression exclusively in eukaryotes, particularly, the invention employs genetically engineered bacterial cells, the native chromosomal genome of which has been irreversibly altered. The alteration may consist of a modification of one or more chromosomal genes which alone or in combination are essential for cell viability in the conditions under which the bacterial cells are propagated or may consist of the insertion of one or more foreign genes that are detrimental to bacterial cell viability under such conditions.

The bacterial cells are then further modified by inclusion of a recombinant plasmid, preferably a high-copy-number recombinant plasmid (a type which occurs in a relatively high number of copies, from 50 to several hundred, per plasmid-harbouring bacterial cell). The recombinant plasmid is constructed to include genetic material which complements the above-mentioned chromosomal alteration. The introduction of the recombinant plasmid into the bacterial cells restores viability of the bacterial cells and ensures that only bacterial cells harbouring the recombinant plasmid can survive.

If the plasmid is to be employed for the production of an expression system operable only in eukaryotes for a foreign, desired DNA, the complementary genetic material must relate to one or more genes that have no functional or structural equivalent in the eukaryotic cells which are to be treated with the plasmid DNA. The complementary genetic material must not encode a polypeptide (or produce an mRNA) capable of acting upon any cell component of the eukaryotic cells which are to be treated with the plasmid DNA. Furthermore, any factors or materials produced as a result of the presence of the complementary genetic material must be incapable of being secreted by, or of being produced at levels which are toxic for, the genetically engineered bacterial cells.

Thus, the complementary genetic material serves to ensure structural and genetic stability of the genetically engineered bacterial cells, by exerting selective pressure for survival only of plasmid-harbouring bacterial cells. As stated above, the plasmid is preferably, but not necessarily, a high-copy number plasmid.

By cloning one or more foreign genes on the same recombinant plasmid, the genetically engineered bacterial cells can be used to produce large quantities of the plasmid DNA containing the foreign gene(s) for use in DNA immunization and gene therapy, including antisense therapy. The foreign genes preferably are incapable of being expressed in the genetically engineered bacterial cells, so as to avoid unnecessary metabolic burden or cell toxicity. This can be accomplished by operatively linking each foreign gene to a promoter functional only in eukaryotes.

Depending upon the foreign gene(s) cloned on the recombinant plasmid, the plasmid DNA can be used in DNA immunization and/or gene therapy. The plasmid DNA can be used for in vivo treatment, to convey one or more desired foreign genes to a eukaryotic host. For example, the foreign gene may be a mammalian gene encoding a polypeptide required for the health or survival of a treated mammal. Or, the foreign gene may be a viral gene encoding a polypeptide against which it is desired to induce immunity in a treated animal. Alternatively, the expression system contained in the recombinant plasmid may produce an antisense mRNA for therapeutic treatment. Other examples will be apparent to those skilled in the art.

The invention will now be further described with reference to various preferred embodiments. However, the invention is not restricted to these embodiments, and one skilled in the art will readily appreciate alternative embodiments within the scope of the description of the features of the invention.

One embodiment depends upon an amino-acid adding enzyme required for the production of the bacterial cell wall.

Peptidoglycans are cell wall structures unique to bacterial cells. Accordingly, some of the genes encoding enzymes responsible for the biosynthesis or assembly of the peptidoglycan layer are excellent candidates for use as marker genes in recombinant plasmids intended for use in DNA immunization and gene therapy.

The peptidoglycan layer consists of several adjacent chains. Each chain consists of alternating units of N-acetylmuramic acid (NAM) and N-acetylglucosamine (NAG) residues. Certain NAM residues on each chain are attached to a tetrapeptide whose composition varies slightly depending on whether the bacteria is Gram positive or Gram negative. The adjacent peptidoglycan chains are linked together by a peptide bond that links the third amino acid, diaminopimelic (dap), of one tetrapeptide to the fourth amino acid, D-alanine, of the tetrapeptide attached to the NAM residue on the adjacent chain. The amino acid D-alanine is a unique component of the peptidoglycan of all bacteria. This amino acid is synthesized from L-alanine by the action of the enzyme designated alanine racemase (alr). The formation of this latter peptide linkage is crucial to bacterial cell viability since in its absence the bacterial cells lyse in commonly used bacterial growth media.

Tetrapeptide formation requires the action of two different sets of genes, namely those that encode enzymes required for the biosynthesis of the individual amino acids of the tetrapeptides (e.g. enzymes required for biosynthesis of L-alanine, D-glutamic acid, dap and D-alanine) and those that are required for the sequential addition and ligation of these amino acids to one another to form the tetrapeptide. The latter enzymes are called amino acid-adding enzymes. In general, the tetrapeptide sequence in the N→C direction is L-alanine/D-glutamic acid/diaminopomelic acid (dap)/D-alanine (SEQ ID NO: 2). The series of amino acid-adding enzymes comprises the L-Ala adding enzyme that adds the amino acid L-alanine to the polysaccharide chain; the enzyme that adds the amino acid D-glutamic acid to the polysaccharide-linked L-alanine (murD) the enzyme that adds the amino acid dap to the L-alanine/D-glutamic acid dipeptide (murE), and the enzyme that adds D-alanine to the L-alanine/D-glutamic acid/dap tripeptide (murF).

Consequently, in one embodiment of the present invention, a system for production of plasmid DNA suitable for use in DNA immunization and gene therapy can be constructed by genetically engineering bacterial cells so as to render nonfunctional a chromosomal gene encoding one of the amino acid-adding enzymes (e.g. the murF gene). The viability of the genetically engineered bacterial cells is ensured by inclusion of a recombinant plasmid on which is cloned a functional murF gene.

Temperature-sensitive bacterial cells are known that contain a mutation in the gene encoding one of the amino acid-adding enzymes (e.g. murF). These cells cannot grow at nonpermissive temperatures, although they can synthesize the individual amino acid components of the tetrapeptide. The inability of these mutants to grow at nonpermissive temperatures is due to the fact that they cannot assemble a complete and functional tetrapeptide at this temperature. Thus, additional suitable bacterial host cells for use in the cell cultures of the present invention would include such existing strains cultured at nonpermissive temperatures.

There are several advantages to the use of the murF gene in the resulting system comprising genetically engineered bacterial cells including complementary recombinant plasmids. First, the murF enzyme is an intracellular and non-diffusible protein, and does not generate a product that is either toxic or secreted. Thus reduction in the number of plasmid-harbouring bacterial cells because of the cross-feeding effect described previously is avoided. Second, the murF gene is unique to bacterial cells and has no functional or structural counterpart in eukaryotic cells, as demonstrated specifically for human cells below. Third, the murF gene has no substrate in eukaryotic cells. Thus there seems to be no risk of activity of the murF enzyme even if the murF gene were expressed in eukaryotic cells treated with the plasmid DNA. These advantages result in efficient recombinant plasmid stabilization and production under industrial fermentation conditions. Furthermore, the murF-based system is safe for use in DNA immunization and gene therapy.

Any of the four amino acid-adding enzymes discussed above can be used as the basis for the complementation system useful in the present invention. Thus, one can alter the bacterial genome to delete the gene encoding the L-alanine-adding enzyme and furnish the gene encoding this enzyme on the plasmid; or the chromosome can be modified to disable it from synthesizing murD, murE or murF and supply the ability to produce the corresponding enzyme on the plasmid.

Although any one of these amino acid-adding enzymes can be chosen, there is a hierarchy which leads to a preferential selection of murF>murE>murD>L-Ala-adding enzyme. This is an efficiency-based consideration grounded in the manner in which cell wall degradation occurs when bacteria divide. Degradation inevitably takes place starting at the C-terminus of the tetrapeptide and may be incomplete. Thus, the daughter cells generally need the murF component more desperately than they need murE, which is in turn more desperately needed than murD or L-alanine-adding enzyme.

A second embodiment depends on rendering nonfunctional a chromosomal gene encoding an enzyme responsible for the synthesis of an amino acid that is present naturally in commonly used bacterial media used in an industrial setting. Generally, such a chromosomal gene alteration is not a practical method for enhancing recombinant plasmid stability nor for high-level production of plasmid DNA. However, when additional safety precautions are incorporated, as exemplified below, this approach can be used for stable plasmid DNA production on an industrial scale.

For example, a chromosomal gene (designated lysA) which encodes an enzyme essential for the synthesis of the amino acid lysine is rendered nonfuctional. A second chromosomal gene (designated lysP) encoding a permease protein that is responsible for uptake of that amino acid from the environment or growth medium is also rendered nonfunctional. Such genetically engineered bacterial cells can no longer survive on their own. They can survive when transformed with a recombinant plasmid carrying a functional gene for or equivalent to lysA or lysP. Thus, a genetically engineered bacterial cell that is defective in lysine uptake (due to a nonfunctional chromosomal lysP gene) and lysine biosynthesis (due to a nonfunctional chromosomal lysA gene) transformed with a recombinant plasmid carrying a functional or equivalent of lysA gene provides an efficient system for stable and high level production of plasmid DNA for DNA immunization and gene therapy.

The plasmid-borne complementation gene in this example is the lysA gene since it is known that lysA gene has no structural or functional counterpart in eukaryotic cells. Furthermore, the lysA enzyme encoded by the lysA gene has no substrate in eukaryotic cells and as such this enzyme cannot function in eukaryotic cells even if it is expressed therein. Since lysine is an essential amino acid for all living microorganisms, including both Gram positive and Gram negative bacteria, this system provides a practical and versatile system for stable and high level production of plasmid DNA in any bacterial cell.

In a third embodiment, selective pressure is maintained by using a postsegregational killing mechanism. The naturally occurring *E. coli* plasmids R1 and F contain genetic loci appropriate for this approach. For the R1 plasmid, this locus is parB (Gerdes, K. et al. *PNAS* (1986) 83: 3116–3120; Rasmussen, P. B. et al. *Mol Gen Genetics* (1987) 209: 122–128). In the case of the F plasmid, this locus is Flm (Loh, S. M. et al., *Gene* (1988) 66: 259–268). These loci mediate efficient recombinant plasmid stabilization by means of a postsegregational killing mechanism.

Both the parB and Flm loci consist of two small genes referred to as the hok (host killing) and sok (suppressor of host killing) genes in the case of parB, and flmA (host killing) and flmB (suppressor of host killing) in the case of the F plasmid. Thus, the hok and flmA genes are analogous in structure and function, and this hok and flmB genes are analogous in structure and function.

The hok and flmA gene products are small hydrophilic proteins (52 amino acids) that are potent host killing factors. The expression of hok gene is regulated by a small (about 100 base pairs) RNA molecule transcribed from the sok gene and which acts as an antisense RNA complementary to the mRNA of the hok gene. Similarly, the expression of the flmA gene is regulated by an approximately 100-base pair RNA molecule transcribed from the flmB gene which acts as an antisense RNA complementary to the mRNA of the flmA gene. The hok and flmA mRNAs are highly stable, whereas the sok and flmB RNAs are rapidly degraded. It is the differential stability of the two RNA species in each case which results in the mechanism of bacterial cell killing. When a bacterial cell containing a plasmid with the parB locus loses such a plasmid, the prolonged persistence of the hok mRNA leads to synthesis of hok protein, thus ensuring a rapid and selective killing of newly formed plasmid-free bacterial cells. Similarly, when a bacterial cell containing a plasmid with the Flm locus loses the plasmid, the prolonged persistence of the flmA mRNA leads to the synthesis of the flmA protein, thus ensuring rapid and selective killing of newly formed plasmid-free bacterial cells.

The combined effect of hok and sok genes or of the flmA and flmB genes can be used to advantage in constructing a system for use in plasmid DNA production for use in DNA immunization and gene therapy. The utility of these systems could be hampered by the potential for killing eukaryotic cells such as those of mammalian hosts injected with plasmid DNA containing the hok/sok or flmA/flmB combination during DNA immunization or gene therapy. Accordingly, only the sok gene (100 bp) or flmB gene (100 bp) is included in the recombinant plasmid, whereas the hok gene or flmA gene is integrated in the bacterial cell chromosome.

For the plasmid production system based on the hok/sok or flmA/flmB combination, a bacterial strain is genetically engineered in which the gene encoding the hok or flmA protein is inserted in a non-essential region of the bacterial chromosome (e.g. in the lacZ gene). Genetically engineered bacterial cells are then transformed with a recombinant plasmid in which the only marker is the corresponding sok or flmB gene. So long as the recombinant plasmid remains in the bacterial cells, the sok or flmB gene on the recombinant plasmid serves to regulate the expression of the hok or flmA gene and the bacterial cell thrives. As soon as the recombinant plasmid carrying the sok or flmB gene is lost, the bacterial cell dies because of the killing factor produced by the chromosomal hok or flmA gene.

This system offers the following specific advantages for production of plasmid DNA. First, the system is not limited in its use to a particular bacterial strain. Second, since only 100 bp of DNA encoding the sok or flmB gene will be used in the recombinant plasmid, a much smaller and more compact plasmid can be constructed. This lends itself to higher plasmid yield and provides the ability to clone more than one foreign gene on the recombinant plasmid.

One skilled in the art will appreciate other combinations according to the invention of genetically engineered bacterial strains and recombinant plasmids (which can serve as a vector for foreign DNA) wherein the recombinant plasmid includes DNA complementary to the altered (i.e. added or rendered nonfunctional by modification, deletion, or inactivation) chromosomal DNA and which accordingly serves as a marker for presence or absence of the recombinant plasmid, as well as selective pressure to maintain the recombinant plasmid in the genetically engineered bacterial cell.

The present invention will be illustrated in detail in the following examples. These examples are included for illustrative purposes, and should not be considered to limit the present invention.

EXAMPLE 1

Construction of Chromosomally Altered Host CB102

The peptidoglycan layer is absolutely required for bacterial cell viability under ordinary circumstances, as it protects the fragile cytoplasmic membrane from osmotic shock. However, under certain circumstances, bacterial cells that have a defect in peptidoglycan synthesis can still survive in certain types of media such as those supplemented with sodium chloride or sucrose. The reason for the ability of these bacterial cells to survive in these types of media is attributed to the action of these supplementary compounds as osmotic stabilizers or due to their ability to induce colanic acid production which acts as an osmotic stabilizer. Thus, in a preferred embodiment bacterial cells are genetically engineered so as to be absolutely dependent on the presence of an intact peptidoglycan layer regardless of the type of media in which the bacterial cells are grown. The ability of these bacterial cells to synthesize colanic acid is, in this embodiment, abolished in addition to introducing a mutation or a deletion that results in a defective peptidoglycan assembly.

Colanic acid is a polymer composed of glucose, galactose, fucose, and glucuronic acid. Since galactose is one of the colanic acid components, one way to abolish the ability of bacterial cells to produce colanic acid is to inhibit the ability of bacterial cells to synthesize and utilize galactose. In this example, this is achieved by introducing irreversible deletions in the galE and galT chromosomal genes involved in galactose utilization. The resulting bacterial strain is then subjected to a deletion in the murF chromosomal gene to produce a strain whose viability is dependent on complementation with a recombinant plasmid carrying a functional murF gene, as follows:

First, the JM105 *E. coli* strain containing a deletion in the galE and galT genes was constructed. To clone the galE and galT genes, two oligonucleotide primers (upstream and downstream) were synthesized based on the known nucleotide sequences of the galE and galT genes. To facilitate cloning, an XbaI site was engineered at the end of each of these primers. The upstream primer (designated gal-3) corresponded to the 5' end of the galE gene and had the following nucleotide sequence (SEQ ID NO: 3):

5'gctctagaggctaaattcttgtgtaaacga3.

The downstream primer (designated gal-4) corresponded to the 3' end of the galT gene and had the following nucleotide sequence (SEQ ID NO: 4):

5'gctctagatctgccagcatttcataaccaa3'.

Primers gal-3 and gal-4 (100 pmoles each) were combined with 2 µl of an overnight culture of JM105 bacterial cells. To this mix was added 4 µl of a 5 mM deoxynucleoside (dNTP's) solution, 1 µl of 100 mM $MgSO_4$, 5 µl of 10X Vent reaction buffer and 1 µl of Vent DNA polymerase (purchased from NEB Biolab). The reaction mix was amplified for 30 cycles using a cycling profile as follows: Melting: 94°C for 1 minute, Annealing: 55°C for 1 minute, and Extension: 72°C for 2 minutes. Following amplification, the reaction mix was analyzed by electrophoresis through 1% agarose. A single band of the expected size (approximately 2 Kilobase pairs; corresponding to the entire galE and galT genes) was evident following ethidium bromide staining of the DNA present in the polymerase chain reaction (PCR) reaction mix. The above DNA band was excised and purified away from the agarose using the GeneClean kit (obtained from BioCan). As illustrated in FIG. 1, the purified DNA fragment was treated with T4 polynucleotide kinase (Pharmacia) and ligated into the HincII site of pTZ18 plasmid. pTZ18 plasmid containing the galE and galT genes was designated pCB233.

An internal deletion within galE and galT genes was constructed as further illustrated in FIG. 1. A pTZ18 plasmid was cut with HindIII enzyme, treated with Klenow enzyme, and self-ligated to produce plasmid pCB234 in which the HindII site no longer existed. Plasmid pCB233 was cut with EcoRI and PstI enzymes to retrieve a DNA fragment encompassing the entire galE and galT genes. This latter fragment was ligated into pCB234 that was also cut with EcoRI and PstI enzymes. The ligation event led to the isolation of a plasmid designated pCB235. Plasmid pCB235 was cut with HindIII and NcoI enzymes to delete an internal portion of the nucleotide sequence within the galE and galT sequences, treated with Klenow enzyme, and then self-ligated to produce plasmid pCB236. Plasmid pCB236 was cut with EcoRI and PstI enzymes to retrieve the shortened galE and galT genes. The DNA fragment encompassing the shortened galE and galT genes was treated with T4 DNA polymerase enzyme. At the same time, the suicide vector plasmid designated pCVD442 (J. B. Kaper; University of Pennsylvania) was cut with XbaI enzyme and then treated with Klenow enzyme. The DNA fragment encompassing the shortened galE and galT genes was then ligated into the above pCVD442 and transformed into *E. coli* SY327 to produce plasmid pCB237. Plasmid pCB237 was then transformed into *E. coli* SM10 and the latter bacterial cells containing pCB237 were selected for further use as described below.

Figure 2:
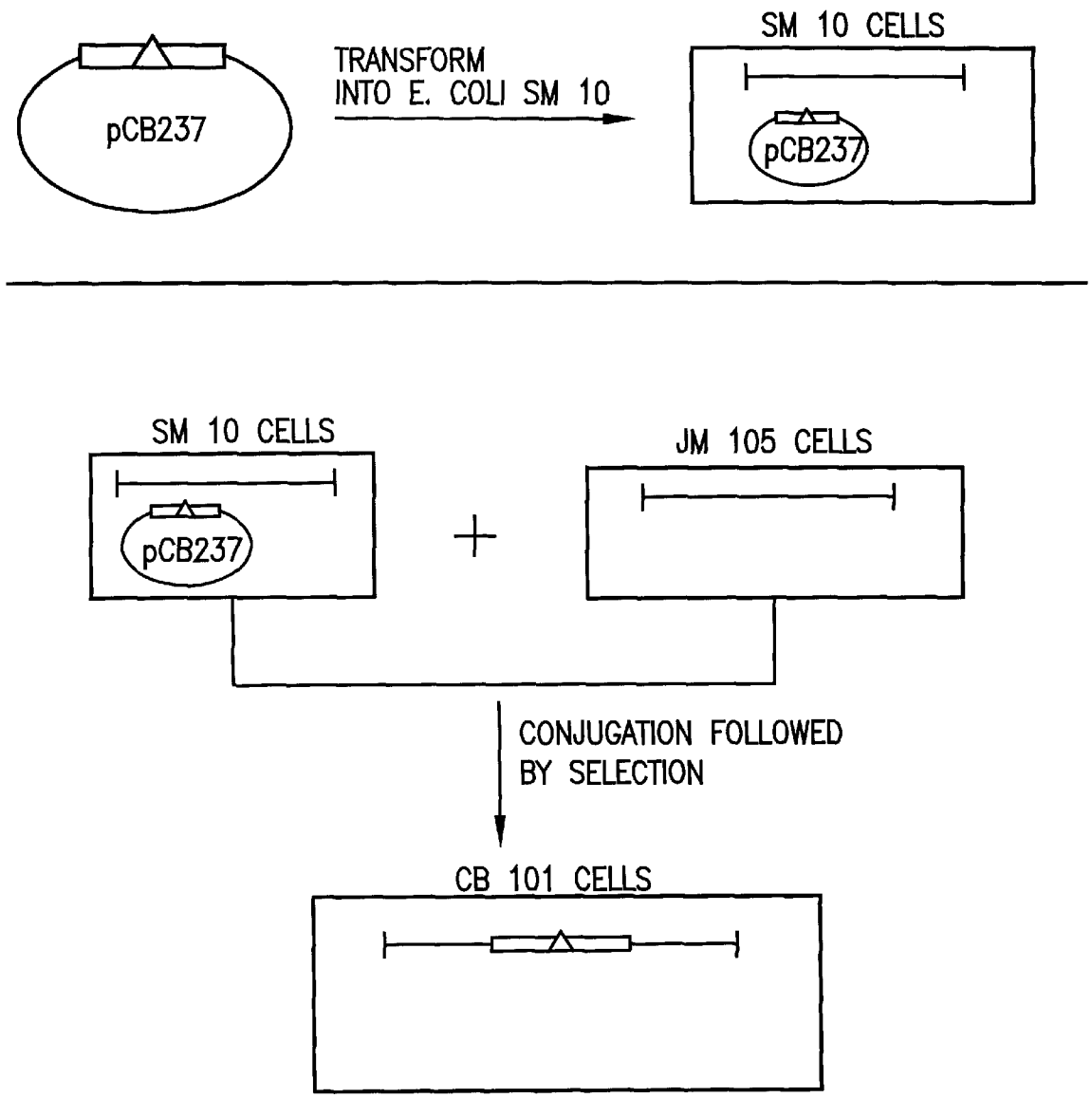
FIG. 2 shows the construction of a genetically engineered bacterial strain (CB101 *E. coli*) having a deletion in the chromosomal galE and galT genes.

The galE and galT deletions were introduced into JM105 *E. coli* as illustrated in FIG. 2. SM10 bacterial cells carrying plasmid pCB237 were used to transfer the irreversibly nonfunctional (i.e. with internal deletion) galE and galT genes into *E. coli* strain JM105 by the conjugation protocol described by Donnenberg, M. and Kaper, *J Infection and Immunity* (1990) 59: 4310–4317. The incorporation of the irreversibly nonfunctional galE and galT genes into the chromosome of JM105 bacterial cells and the replacement of full-length wild type galE and galT genes of the latter bacterial cells with the irreversibly nonfinctional galE and galT genes was verified by PCR analysis of JM105 chromosomal DNA. The JM105 E. coli bacterial strain containing an internal deletion in galE and galT genes was designated CB101.

To produce a deletion in the murF locus, first the chromosomal murF gene from JM105 E. coli was isolated using the polymerase chain reaction (PCR). Two oligonucleotide primers were synthesized based on the known sequence of the murF gene. These primers were designated murF1 and murF2 and their nucleotide sequences were as follows:

Upstream primer (murF1) (SEQ ID NO: 5):
5'cgagcactgcgagagatgattagcgtaacccttagccaactt3' and Downstream primer (murF2) (SEQ ID NO: 6):
5'cagcgcgtgcagcaggctgacagtggcgcga3'.

The murF gene appears to be transcribed under the control of the murE promoter, consequently the above PCR primers were designed so as to allow inframe fusion of the murF coding sequence to the murE promoter. For this purpose, the murE gene including its promoter element was isolated from JM105 E. coli using PCR primers designated murE1 and murE2. The nucleotide sequences of these primers were as follows:

Upstream primer (murE1) (SEQ ID NO: 7):
5'gccggatccgcgccggtctggtgcca3', and

Downstream primer (murE2) (SEQ ID NO: 8):
5'aagggatccgctaatcatgcaatcacc3'.

Figure 3:
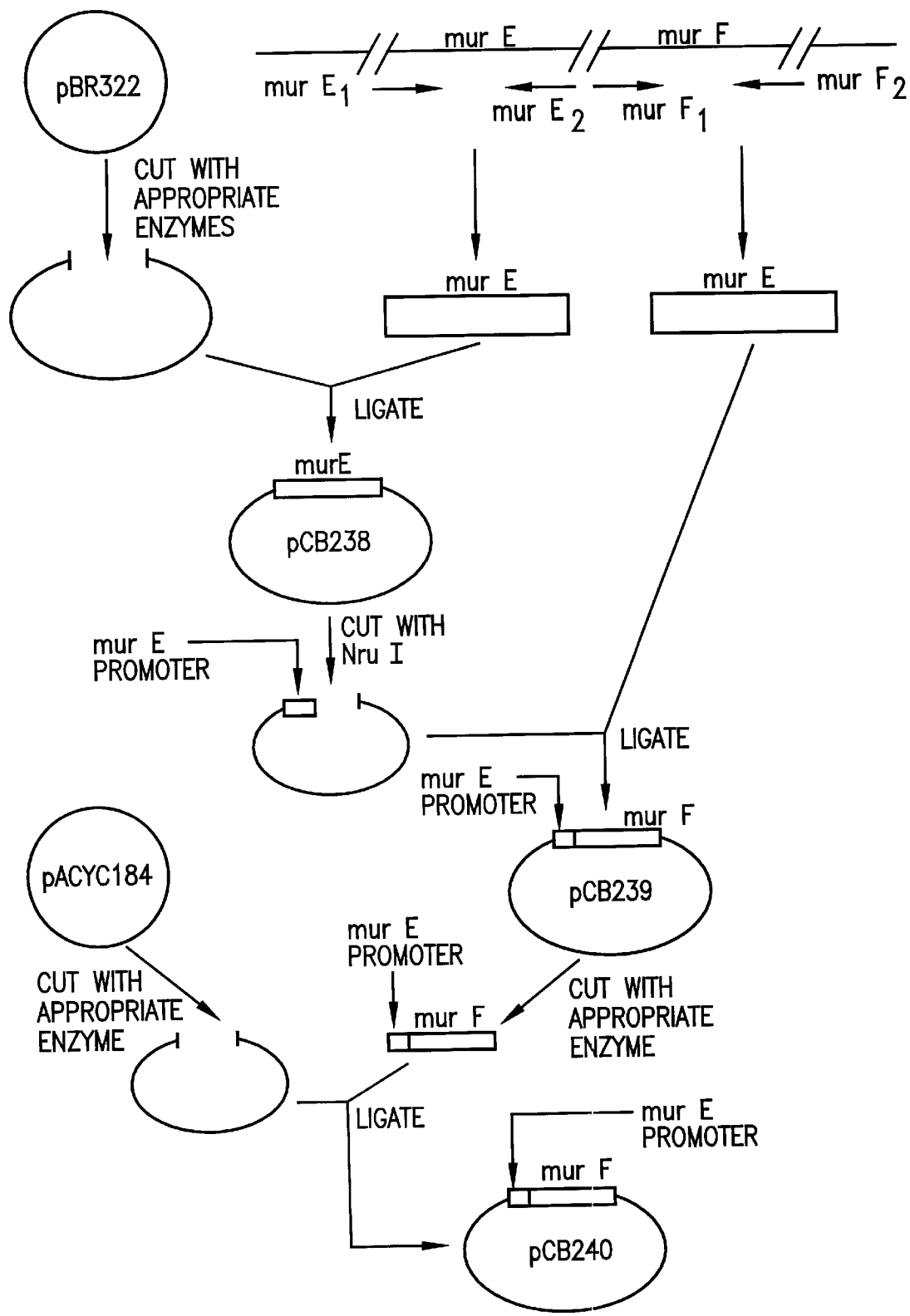
FIG. 3 is a schematic showing the cloning of the murF gene.

As illustrated in FIG. 3, following PCR amplification, the murE gene was cloned into plasmid pBR322 to produce a plasmid designated pCB238. The murF gene was amplified from JM105 bacterial cells using primers murF1 and murF2. Plasmid pCB238 was digested with NruI enzyme to remove the murE gene coding sequence, leaving behind the murE promoter sequences. The amplified murF gene was then ligated to the plasmid pCB238 that had been digested with NruI enzyme and the resulting plasmid was designated pCB239.

Plasmid pCB239 is digested with appropriate enzymes to excise a DNA fragment encompassing the murE promoter fused to the murF gene, and the fragment is then cloned into plasmid pACYC184 to produce plasmid pCB240.

In order to construct an E. coli strain with an irreversible alteration (i.e. deletion) in its murF gene, a plasmid in which a deleted murF gene is cloned along with DNA sequences derived from upstream and downstream flanking sequences is constructed. For this purpose, an oligonucleotide primer is designed based on the known sequences of the murE gene (upstream of murF gene) and a second oligonucleotide primer is designed on the basis of the known sequence of the OrfY gene (downstream of the murF gene). The upstream primer is designated murE1 and had the following nucleotide sequence (SEQ ID NO: 7):

5'gccggatccgcgccggtctttggtgcca3'.

The downstream primer is designated OrfY-1 and has the following nucleotide sequence (SEQ ID NO: 9):

5'taacgccagcgaacctacatc3'.

Figure 4:
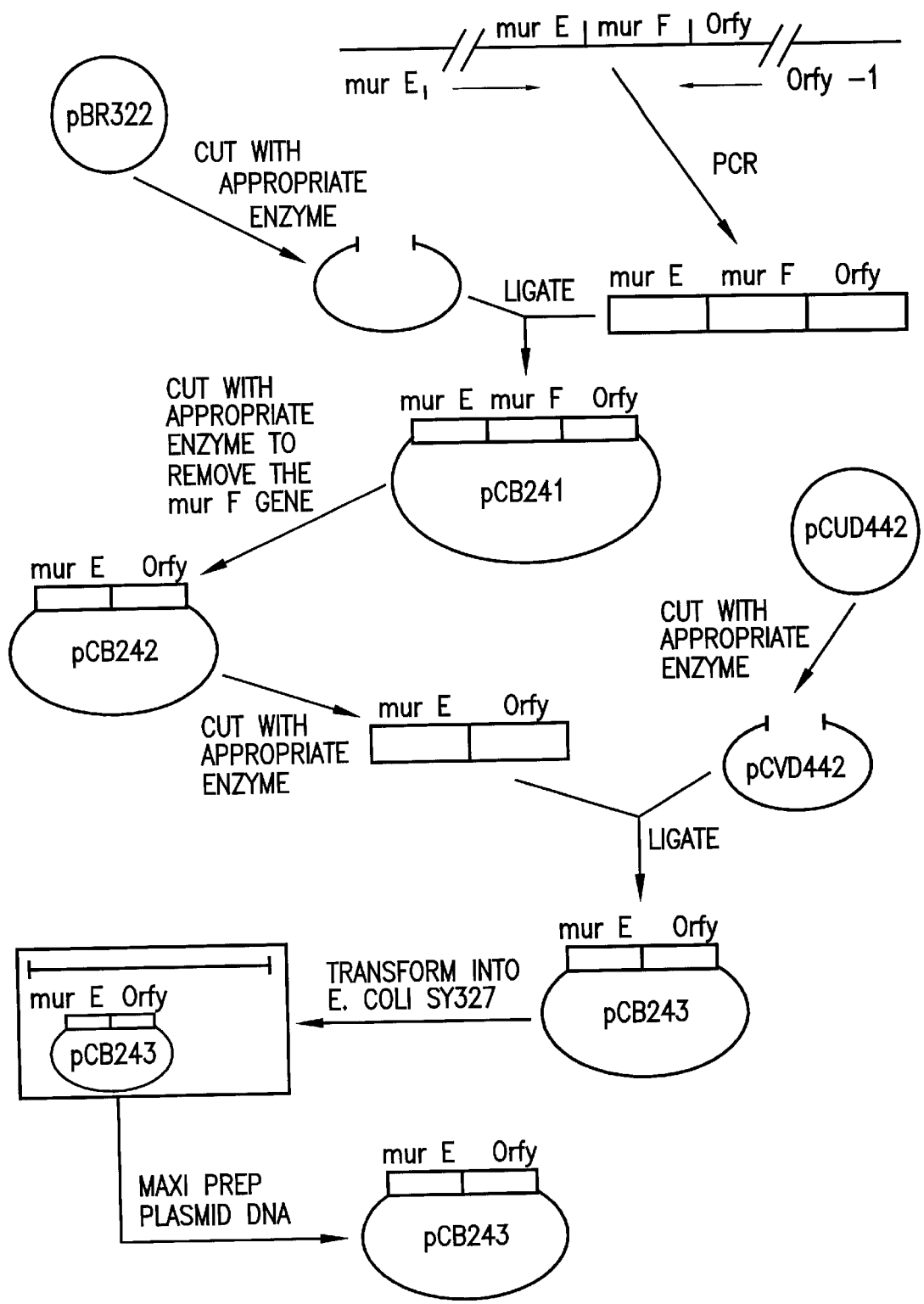
FIG. 4 shows the construction of the recombinant plasmid pCB243.

Primers murE1 and OrfY-1 are used in the PCR reaction to amplify the murF gene with flanking sequences derived from the murE and the OrfY gene. As illustrated in FIG. 4, the amplified DNA fragment is cloned in plasmid pBR322 to produce plasmid pCB241. Plasmid pCB241 is digested with appropriate enzymes to remove most of the murF gene leaving only a small portion of the murF gene sequence flanked by a sequence derived from the murE gene on one side and a sequence derived from the OrfY gene on the other side. Following digestion, the plasmid is self-ligated to produce plasmid pCB242. The DNA fragment encompassing the sequences derived from the murE part of murF and OrfY genes is retrieved from plasmid pCB242 by digestion of the latter with appropriate enzymes. The DNA fragment carrying the latter sequences is then ligated into the suicide vector pCVD442 and transformed into SY327 E. coli cells. The latter bacterial cells are used to prepare plasmid pCVD442 containing the flanking sequences and this latter plasmid is designated pCB243. Plasmid pCB243 is then transformed into E. coli SM10 cells to produce a population of bacterial cells suitable for use in transfer of the murF deletion into the E. coli strain CB101.

Figure 5:
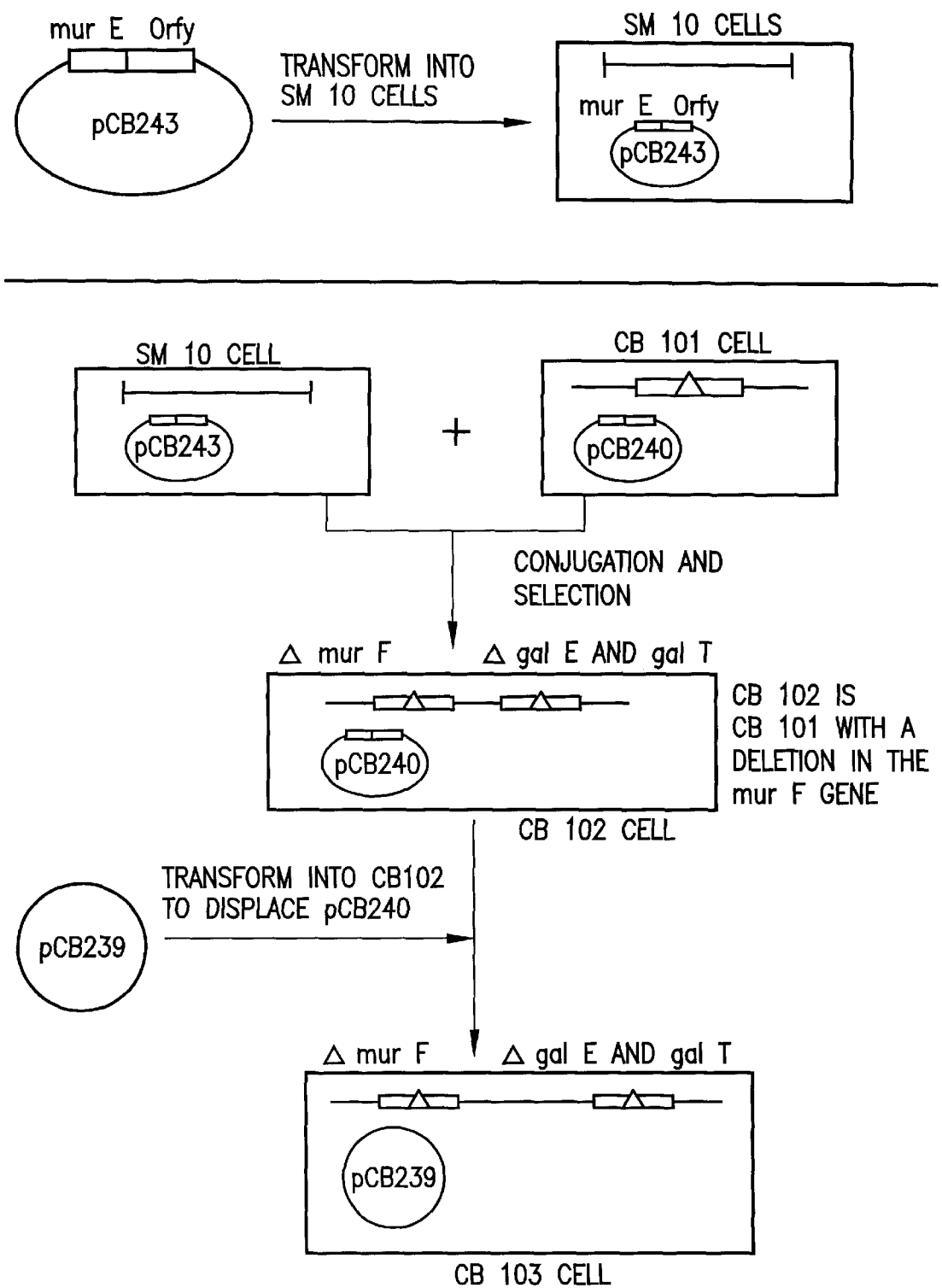
FIG. 5 shows the construction of a genetically engineered bacterial strain (CB1031 *E. coli*) having a deletion in the chromosomal murF gene.

As illustrated in FIG. 5, SM10 bacterial cells carrying plasmid pCB243 are used to transfer the irreversibly nonfunctional (i.e. with internal deletion) murF gene into E. coli strain CB101 transformed with plasmid pCB240 by the conjugation protocol described above (Donnenberg and Kaper 1990). The incorporation of the irreversibly altered murF gene into the chromosome of CB101 bacterial cells and the replacement of full-length wild type murF gene of the latter bacterial cells with the irreversibly altered murF gene is verified by PCR analysis of CB101 chromosomal DNA. The CB101 bacterial strain containing an internal deletion in the murF gene is designated CB102.

Bacterial strain CB102 can then be transformed with plasmid pCB239 to displace plasmid pCB240. Bacterial strain CB102 carrying plasmid pCB239 is designated CB103.

EXAMPLE 2

Construction of an Alternative murF Deficient Bacterial Host, TK-48

Certain temperature-sensitive bacterial cell mutants containing a mutation in the murF gene, such as TKL-46, can grow at 30° C., but cannot grow at the nonpermissive temperature of 42° C. The inability of these mutants to grow at nonpermissive temperatures is due to the fact that they cannot assemble a complete and functional cell wall tetrapeptide due to the mutation in the murF gene. These mutants can be used as bacterial hosts in the cell culture systems of the invention.

A system for production of recombinant plasmids suitable for use in DNA immunization and gene therapy can thus be constructed by inclusion, in these temperature-sensitive bacterial cells (e.g. E. coli strain TKL-46 or its derivatives), of a recombinant plasmid containing a murF gene functional at 42° C. By growing the bacterial cells at 42° C., only cells carrying the recombinant plasmid can survive.

In this example, a more preferred derivative of TKL-46, useful as a host, was prepared. E. coli strain TKL-46 (Lugtenberg et al., J Bacteriology (1972) 110: 35–40) was obtained from Coli Genetic Stock Center (CGSC). TKL-46 bacterial cells were first grown at 30° C. in LB broth containing the antibiotic nalidixic acid to select for a nalidixic acid-resistant strain, designated TKL-47. TKL-47 cells were rendered recA-negative by conjugation with the (nalidixic acid-sensitive, recA-negative) bacterial strain JC10240 in order to abolish the ability of the cells to perform homologous recombination. Thus their chromosomes will not acquire any genetic material from introduced plasmid DNA. RecA-negative cells derived from TKL-47 cells were designated TKL-48.

TKL-48 bacterial cells were grown at 30° C. and then used for preparation of competent bacterial cells. Competent TKL-48 bacterial cells are transformed with plasmid pCB239 carrying a functional murF gene to produce a bacterial strain designated TKL-49. TKL-49 bacterial cells are then grown at 42° C. as a method for recombinant plasmid maintenance and plasmid DNA production.

As an alternative to CH102 or TKL-48 bacterial cells as hosts, additional improved forms are constructed by modifying the murF gene in the chromosomes of cells that have native qualities that are desirable. For example, some *E. coli* strains are deficient in enzymes, such as endonucleases which degrade plasmid DNA. If the chromosomes of these hosts can be altered to provide, for example, the temperature-sensitive form of murF, these hosts provide advantageous alternatives to TKL-48.

The temperature-sensitive murF gene from TKL-46 was obtained by amplifying the appropriate sequence using PCR with murF3 and murF4 as primers:

murF3 (Upstream primer) (SEQ ID NO: 10):
5'gccggatcccgatcgcgtcacggtggcgcg3' murF4 (Downstream primer) (SEQ ID NO: 11):
5'gaagatctcagcgcgtgcagcaggctgacagtggcgcga3'

The amplified nucleotide sequence was cloned into the BamHI site of pUC19 and the nucleotide sequence was determined using the dideoxynucleotide method. The complete nucleotide sequence of the amplified gene is shown in FIG. 11, and differs from the wild-type gene as positions 862 and 990 as shown in FIG. 11. The replacement of G with A at position 862 results in threonine rather than alanine; the addition of the GAC codon at position 990 results in addition of an aspartic acid residue to the peptide sequence.

The host strain with desirable characteristics is then altered by replacing the wild-type murF gene with the temperature-sensitive form typically by homologous recombination to obtain the improved bacterial host.

Thus, either CB102 or TKL-48 or other desired bacteria modified to contain the temperature-sensitive murF gene, which have irreversible chromosomal mutations in the murF gene, rendering the gene or the encoded murF protein nonfunctional under the culture conditions employed, can be used as suitable hosts where the introduced plasmid has a murF gene functional under the culture conditions employed. The production levels can be compared to production of foreign DNA contained on plasmid pBR322 in which a marker gene encodes ampicillin.

EXAMPLE 3

Construction of Additional murF-Containing Plasmids

Figure 6:
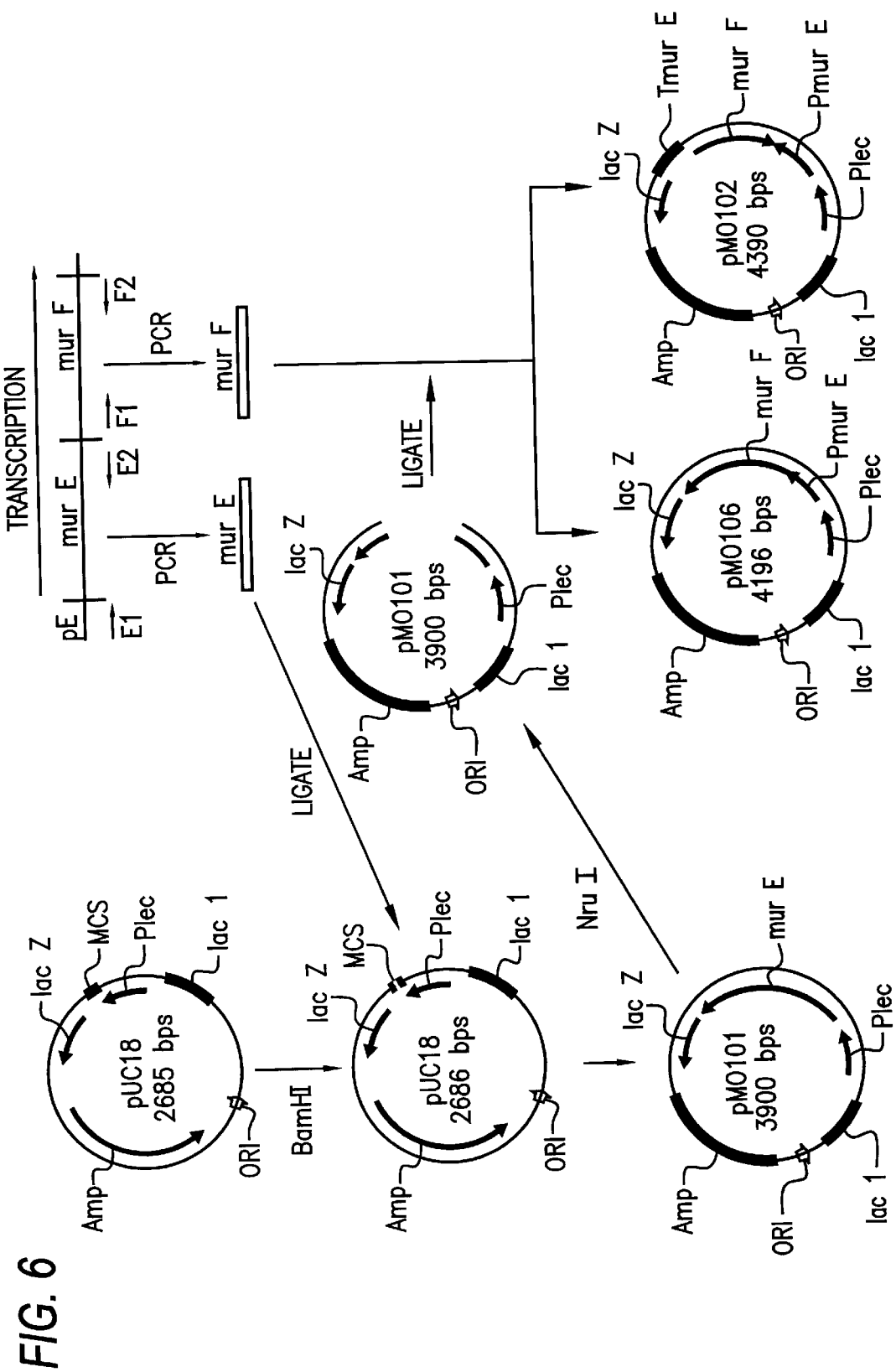
FIG. 6 is a diagrammatic representation of the construction of plasmids containing the murF gene.

Using the murE1 and murE2 primers described in Example 1, the chromosomal murE gene was PCR amplified from *E. coli* JM105 genomic DNA and cloned into the BamHI site of pUC18. The resulting plasmid, pMO101, was cut with NruI which removes most of the murE gene, except for the murE promoter and approximately 330 bp of the murE 3' end. The murF gene, amplified as described in Example 1, was ligated into the NruI site of pMO101, and the ligation mixture transformed into *E. coli* JM109. Two plasmids, designated pMO102 and pMO106 were identified, which contain the murF coding sequence in opposite orientations. pMO106 contains the murF gene in the correct orientation operably linked to the murE promoter and expresses the murF protein; pMO102 contains the wrong orientation for murF, and thus does not express the gene. A summary of the construction of pMO102 and pMO106 is shown in FIG. 6.

Additional plasmids containing the murF gene were constructed as follows:

pHW203 was constructed as a system for testing in vitro transfection efficiency into eukaryotic cells. pCMVB, available from Clonetech, which contains the β-galactocidase gene under control of a promoter operable in mammalian cells was cut with EcoRI, treated with Klenow, and ligated with the BamHI, Klenow-filled fragment from pMO106 that contained the murF gene. The resulting plasmid was cut with BstHI to remove the ampicillin-resistance gene and religated. The religated product was transformed into TKL-48 and an isolated colony, containing the plasmid pHW203, the colony designated TKL-52, was used for large-scale production of the plasmid.

The plasmid pCB253 was constructed in order to evaluate whether the murF gene had any effect on DNA immunization in eukaryotic hosts. The host plasmid, pSLRSVGIV.md1, obtained from R. Braun contains the gene encoding glycoprotein IV (GIV) from bovine herpes virus under control of the Rous Sarcoma Virus promoter; therefore, this plasmid contains an expression system for production of an immunogen in vertebrates. The BamHI DNA fragment from pMO106 containing the murF gene under control of the murE promoter was ligated into the Msc site of pSLRSVGIV.md1 and the ligation mixture transformed into JM109 cells (obtained from New England Biolabs). The plasmid isolated from successful transformants was digested with BstHI to remove the ampicillln resistance gene, religated and then transformed into TKL-48 to obtain the product plasmid pCB253. The pCB253 colony, designated TKL-51, was used for large-scale preparation of this plasmid.

In the foregoing paragraphs, TKL-48 was transformed with pMO102, pMO106, pCB253 or pHW203 by mixing competent cells with plasmid DNA and incubating on ice for 30 min. The cells were then heat-shocked at 42° C. for 90 sec and then incubated in 1 ml of LB broth at 30° C. for 2 hrs. The cells were then plated on LB/0.1% thymine plates and incubated at 42° C. overnight. The transformed cell lines obtained were designated as follows:

pMO102—TKL-49A;
pMO106—TKL-50;
pCB253—TKL-51;
pHW203—TKL-52.

Of course, TKL-49A cells produce the murF gene product only 30° C., and they are used as a control to assess plasmid yield in the presence of ampicillin as the selectable marker at 30° C. Plasmid yield could be assessed at 42° C. without addition of ampicillin for the remaining cell lines.

EXAMPLE 4

Plasmid Yield

TKL-50, -51, and -52 cells were used to assess plasmid yield when cells are grown at 42° C. without addition of ampicillin, TKL-49A cells were used as controls. Single colonies from LB/thymine plates were picked and inoculated into 2 ml of TB/thymine broth and incubated for 6 hr at 42° (30° C. in presence of ampicillin for TKL-49A). Cells were then inoculated into 10 ml TB/thymine broth, grown for four more hours, then inoculated into 250 ml of TB/thymine broth and grown for an additional 12 hr. Plasmids were extracted from cells using Quiagen columns as recommended by the manufacturer, and plasmid yield determined by calculating O.D. 260 and 280. Purity of plasmids was determined by analysis of plasmid aliquote on agarose gels.

Plasmid yield was also determined in a 10-liter fed-batch oxygen enriched fermentation in a 14-liter NBS Microferm apparatus, in TB broth supplemented with 0.01% thymine at agitation speed of 200 rpm, aeration flow of 0.6VVM (6 l/min, 5 psig) and pH maintained at 7.2. Plasmid yield was determined following extraction of plasmid DNA from aliquots of culture medium using the Quiagen column method.

Yields from cells grown in shake flasks (3 preparations) or a 10-liter fermentor (two runs) is shown in Table 1.

TABLE 1

Plasmid yields from cells grown in shake flasks and a 10-liter fermentor

| Strain/Plasmid Combination | Selection Pressure | Absolute Plasmid Yield (mg/liter)[a] | | Specific Plasmid Yield (mg/gm dry weight)[b] |
|---|---|---|---|---|
| | | shake flasks | fermentor | |
| TKL-49/pMO102 | 30° C./Ampicillin | 2.67 ± 0.16 | 43.85 | 3.3 |
| TKL-50/pMO106 | 42° C./murF | 6.13 ± 0.71 | 144 | 6.788 |
| TKL-51/pCB253 | 42° C./murF | 8.61 ± 0.51 | 107 | N/D[d] |
| TKL-52/pHW203 | 42° C./murF | 6.14 ± 2.2 | N/D | N/D |

Figure 7:
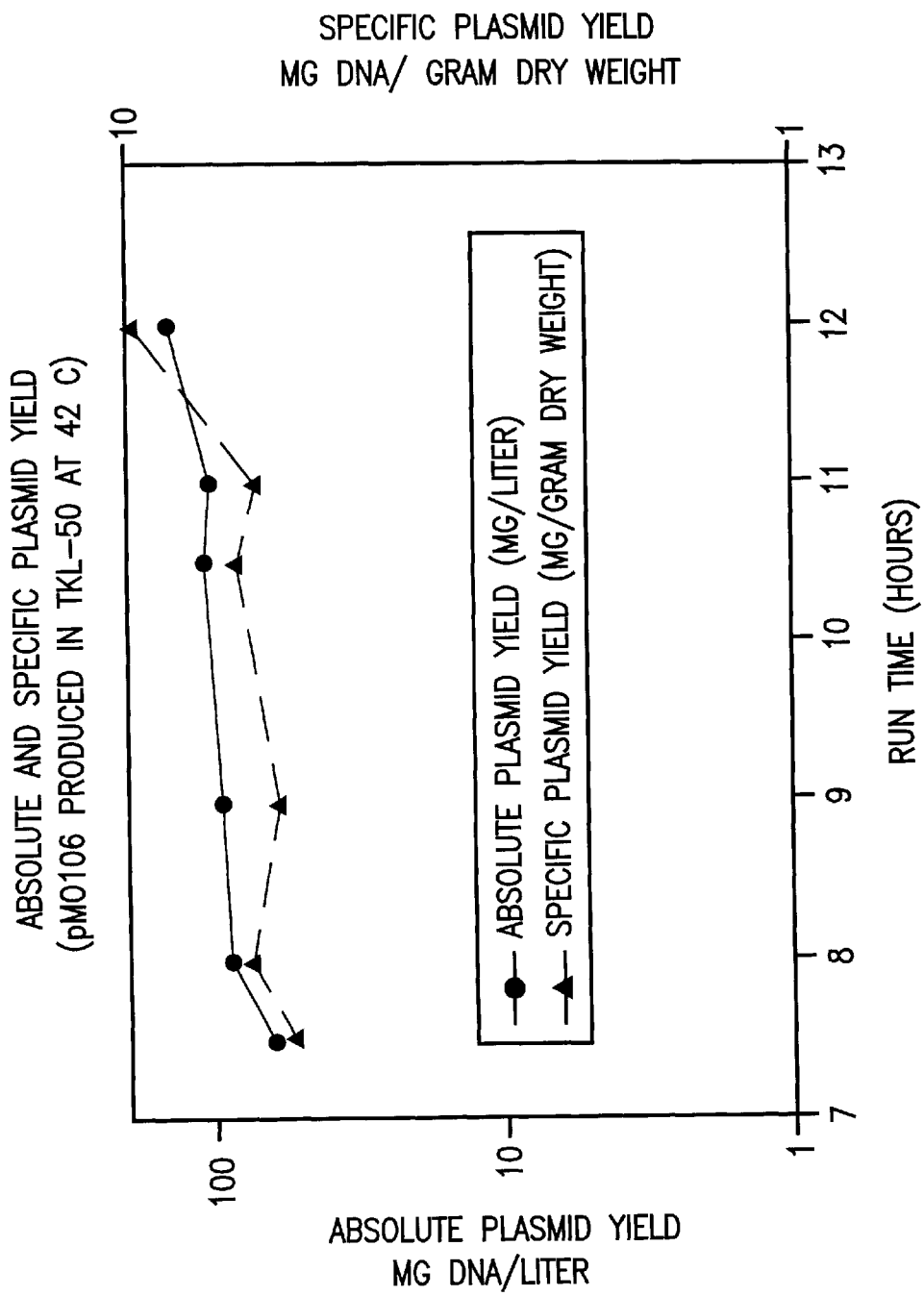
FIG. 7 shows plasmid yields for pMO106 produced in a murF-deficient strain at 42° C.

[a]Plasmid yield from shake flasks and fermentor runs are extrapolated from aliquots of culture volumes (5, 10, and 25 ml) used for preparation of plasmid DNA.
[b]gram dry weight per liter of culture (g/L) was determined from the equation: $g/L = 0.08 + 0.63$ (O.D. 660)
[c]Yield is the average of two fermentations for pMO102 and pMO106. Yield of pCB253 is derived from one fermentation run.
[d]Not Determined FIG. 7 shows the absolute and specific plasmid yield determined for plasmid MO106 produced in TKL-50 strain.

EXAMPLE 5

Plasmid Stability

Stability of plasmid pMO106 in TKL-50 strain was assessed over 170 generations of growth under different selection pressures for plasmid maintenance as follows. Cells were grown in TB/0.1% thymine broth at either 30° C. or 42° C. Samples were taken after different numbers of generations at the relevant temperature, diluted and plated on TB/thymine plates and incubated at 30° C. Colonies were then replicated onto TB/thymine/ampicillin plates and incubated at 30° C. or 42° C. The percent of plasmid-containing cells was determined by comparing the number of colonies growing in the presence and absence of ampicillin at 30° C. or 42° C. Presence of plasmids was further verified by the small scale alkaline lysis method for plasmid preparation.

Figure 8:
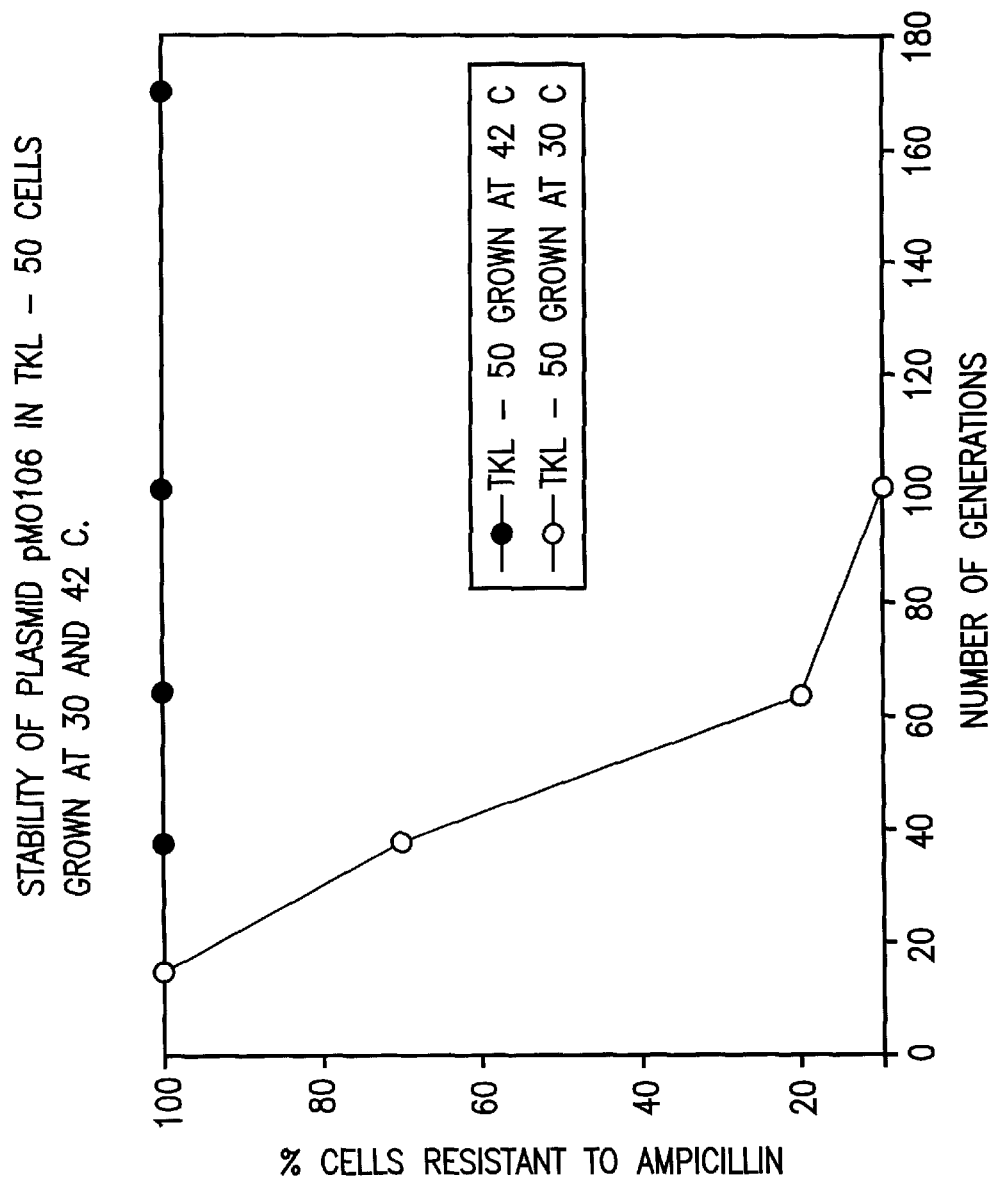
FIG. 8 shows the stability of pMO106 in TKL-50 cells.

Plasmid pMO106 was gradually lost from cells grown at 30° C., but was retained in 100% of the cells grown at 42° C. for 170 generations of growth as shown in FIG. 8. The integrity of plasmid pMO106 was confirmed by restriction analysis.

TKL-49A cells were also tested by growing in the presence of ampicillin at 30° C.; plasmid pMO102 was retained in 100% of the cells for 120 generations.

EXAMPLE 6

Effectiveness of In Vitro Transfection

Plasmid pCMVB and pHW203, described above were used in this assay. 2 µg of each plasmid were mixed separately with varying amounts of lipofectamine (Gibco/BRL) and transfected into the mouse fibroblast L-929 cells according to the manufacturer's recommendation. The efficiency of transfection was determined in an X-gal colorometric assay by counting the number of cells expressing β-galactosidase relative to the total number of cells per well.

Figure 9:
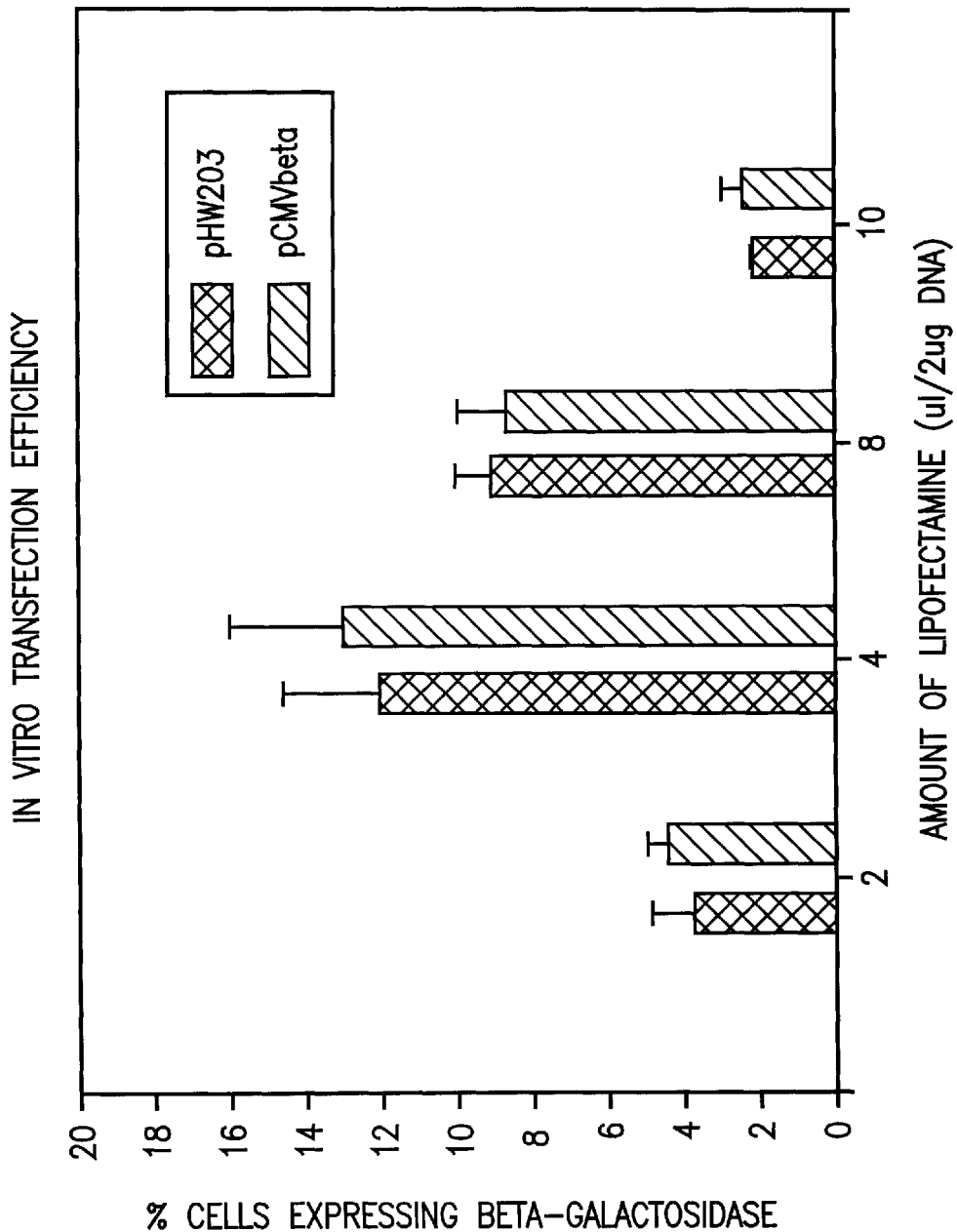
FIG. 9 shows the in vitro transfection efficiency of a vector containing murF.

Similar transfection efficiencies were found for both plasmids as shown in FIG. 9.

EXAMPLE 7

Effect of the murF Gene on Immunization

Figure 10:
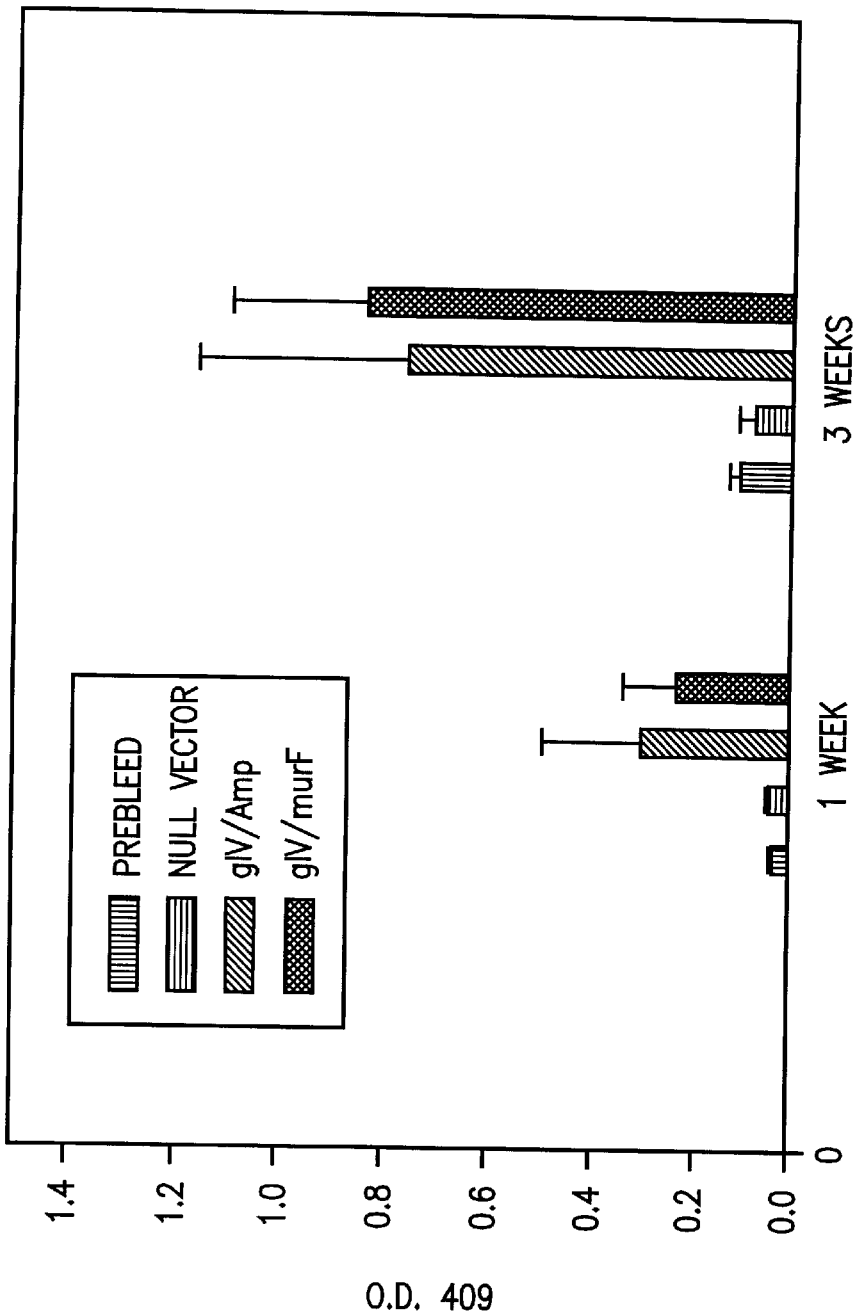
FIG. 10 is a graphic representation of ELISA titers obtained from vectors containing antigens with and without the murF gene.

Groups of ten mice were immunized twice (two weeks apart) intramuscularly with 100 µg each of either plasmid pCB253, pSLRSVG1V.md1 (described above) or with a null vector. At one and three weeks following the second injection, the mice were bled and their sera analyzed for the presence of antibodies specifically immunoreactive for the GIV glycoprotein using an ELISA assay. Similar antibody titers were found in both cases, as shown in FIG. 10.

EXAMPLE 8

Lack of murF Homology to Human Sequences

Searches of nucleotide and amino acid sequence data bases showed that sequences associated with the murF gene/protein have no homology to any known human gene/protein sequences. To confirm this lack of homology, human genomic DNA, purchased from Promega Corporation was digested with EcoRI and BamHI and spiked with pMO106 cut with BamHI. The genomic DNA was electrophoresed in 0.7% agarose gels along with the BamHI fragment containing the murF gene from pMO106, the murF gene coding sequence per se, and an EcoRI linearized plasmid pMO106. After transfer to nylon membranes using capillary transfer, the DNAs were fixed by ultraviolet light cross-linking according to the manufacturer's instructions. The membranes were prehybridized for 8 hours in 6xSSC, 0.5% sodium dodecosulfate at 50° C. and then hybridized for 12 hours with $^{32}$PdCTP labeled full-length murF DNA probe. The blots were washed twice in 2xSSC, 0.5% SDS for 30 minutes at 22° C., followed by two washings for 30 minutes in 1xSSC, 0.5% SDS at 50° C. After drying and exposure to X-ray films for 16 hours-2 weeks, no hybridization signal with human genomic DNA was detected.

I claim:

1. A culture system for stable, high-level production of recombinant plasmids comprising genetically engineered bacterial cells modified to contain said recombinant plasmids, wherein the bacterial cell chromosome is irreversibly modified to effect production of a first substance toxic to bacterial cells, wherein the recombinant plasmid includes genetic material which effects production of a second substance effective to neutralize the toxicity of said first substance under the culture conditions of said culture system, wherein the first substance is the product of the $hok$ gene and the second substance is the product of the $sok$ gene or wherein the first substance is the product of the $flmA$ gene and the second substance is the product of the $flmB$ gene; and wherein the plasmid lacks functional genetic material that encodes said first substance and optionally further includes foreign DNA operatively linked to eukaryotic control sequences whereby said foreign DNA is not expressed in said bacterial cells.

2. The culture system of claim 1 wherein said recombinant plasmid further includes foreign DNA operatively linked to eukaryotic control sequences whereby said foreign DNA is not expressed in said bacterial cells.

3. A method to replicate DNA contained in a plasmid which method comprises culturing the cells of claim 1 or 2 under conditions wherein the viability of said cells is dependent on the presence of said plasmid in said cells.

4. A method to prepare bacterial cells containing replicated plasmid DNA, which method comprises culturing the cells of claim 1 or 2 under conditions wherein the viability of said cells is dependent on the presence of said plasmid in said cells; and recovering the cells.

5. A method to prepare DNA which method comprises culturing the cells of claim 1 or 2 under conditions wherein the viability of said cells is dependent on the presence of said plasmid in said cells, and recovering plasmid DNA from said cells.

6. In a method to provide a desired DNA to an animal host wherein said method comprises administering said desired DNA to said host, the improvement wherein said desired DNA is contained in cells prepared by the method of claim 4.

7. In a method to provide a desired DNA to an animal host wherein said method comprises administering said desired DNA to said host, the improvement wherein said desired DNA is DNA prepared by the method of claim 5.

8. A culture system for stable, high-level production of recombinant plasmids comprising genetically engineered bacterial cells and recombinant plasmids, wherein the bacterial cell chromosome is irreversibly modified so as to render the cell incapable of producing an essential metabolite and also incapable of the uptake of said metabolite from a culture medium, wherein the essential metabolite is lysine, and wherein the inability to synthesize lysine is effected by a mutation in the $lysA$ gene and the inability to take up lysine from the medium is effected by a disruption in the $lysp$ gene, wherein the recombinant plasmid includes genetic material which restores either the ability to synthesize said metabolite or the ability to take up the metabolite from the medium or both and which optionally further includes foreign DNA operatively linked to eukaryotic control sequences whereby said foreign DNA is not expressed in said bacterial cells, wherein said genetic material has no functional or structural equivalent in animal cells; and wherein any protein expressed by said genetic material is incapable of acting upon any animal cell component; and wherein any protein expressed by said genetic material or product resulting from the presence of said protein is not secreted by or toxic to said bacterial cells.

9. The culture system of claim 8 wherein said recombinant plasmid further includes foreign DNA operatively linked to eukaryotic control sequences whereby said foreign DNA is not expressed in said bacterial cells.

10. A method to replicate DNA contained in a plasmid which method comprises culturing the cells of claim 8 or 9 under conditions wherein the viability of said cells is dependent on the presence of said plasmid in said cells.

11. A method to prepare bacterial cells containing replicated plasmid DNA, which method comprises culturing the cells of claim 8 or 9 under conditions wherein the viability of said cells is dependent on the presence of said plasmid in said cells; and recovering the cells.

12. A method to prepare DNA which method comprises culturing the cells of claim 8 or 9 under conditions wherein the viability of said cells is dependent on the presence of said plasmid in said cells, and recovering plasmid DNA from said cells.

13. In a method to provide a desired DNA to an animal host wherein said method comprises administering said desired DNA to said host, the improvement wherein said desired DNA is contained in cells prepared by the method of claim 11.

14. In a method to provide a desired DNA to an animal host wherein said method comprises administering said desired DNA to said host, the improvement wherein said desired DNA is DNA prepared by the method of claim 12.

15. A culture system for stable high-level production of recombinant plasmids comprising genetically engineered bacterial cells and recombinant plasmids, wherein the bacterial cell chromosome is irreversibly altered and the bacterial cells are propagated under conditions such that the viability of the bacterial cells is dependent on the recombinant plasmid, and wherein the plasmid includes genetic material which functionally complements the chromosomal alteration, wherein the chromosome is altered so as to result in the inability of said bacterial cells to synthesize an enzyme that catalyzes a step in the biosynthesis of a cell wall;

wherein said enzyme catalyzes a reaction selected from the group consisting of the addition of L-alanine to a cell wall polysaccharide (L-Ala-adding enzyme); the addition of D-glutamic acid to the L-alanine attached to the polysaccharide chain ($_{murD}$); the addition of dap to the L-alanine/D-glutamic acid dipeptide ($_{murE}$); and the addition of D-alanine to the L-alanine/D-glutamic acid/dap tripeptide of the bacterial cell wall ($_{murF}$);

wherein said genetic material comprises a nucleotide sequence encoding said enzyme;

wherein said genetic material has no functional or structural equivalent in animal cells;

wherein any protein expressed by said genetic material is incapable of acting upon any animal cell component;

wherein any protein expressed by said genetic material or product resulting from the presence of said protein is not secreted by or toxic to said bacterial cells; and wherein the plasmid further includes foreign DNA operatively linked to eukaryotic control sequences whereby the foreign DNA is not expressed in said bacterial cells, but is expressed in animal cells upon delivery of said plasmid.

16. The cell culture system of claim 15 wherein said enzyme catalyzes the addition of D-alanine to the L-alanine/D-glutamic acid/dap tripeptide of the bacterial cell wall ($_{murF}$).

17. A method to replicate DNA contained in a plasmid which method comprises culturing the cells of claim 15 or 16 under conditions wherein the viability of said cells is dependent on the presence of said plasmid in said cells.

18. A method to prepare bacterial cells containing replicated plasmid DNA, which method comprises culturing the cells of claim 15 or 16 under conditions wherein the viability of said cells is dependent on the presence of said plasmid in said cells; and recovering the cells.

19. A method to prepare DNA which method comprises culturing the cells of claim 15 or 16 under conditions wherein the viability of said cells is dependent on the presence of said plasmid in said cells, and recovering plasmid DNA from said cells.

20. In a method to provide a desired DNA to an animal host wherein said method comprises administering said desired DNA to said host, the improvement wherein said desired DNA is contained in cells prepared by the method of claim 18.

21. In a method to provide a desired DNA to an animal host wherein said method comprises administering said desired DNA to said host, the improvement wherein said desired DNA is DNA prepared by the method of claim 19.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
       (A) LENGTH: 1360 base pairs
       (B) TYPE: nucleic acid
       (C) STRANDEDNESS: single
       (D) TOPOLOGY: linear (vi) ORIGINAL SOURCE:
       (A) ORGANISM: Escherichia coli
       (B) STRAIN: TKL-46

(ix) FEATURE:
       (A) NAME/KEY: misc_RNA
       (B) LOCATION: 1..1360
       (D) OTHER INFORMATION: /gene= "murF"

(xi) SEQUENCE DESCRIPTION: SEQ ID NO:1:

```
ATGATTAGCG TAACCCTTAG CCAACTTACC GACATTCTCA ACGGTGAACT GCAAGGTGCA      60

GATATCACCC TTGATGCTGT AACCACTGAT ACCCGAAAAC TGACGAAGGG CTGCCTGTTT     120

GTTGCCCTGA AAGGCGAACG TTTTGATGCC CACGATTTTG CCGACCAGGC GAAAGCTGGC     180

GCGGCAGGCG CACTACTGGT TAGCCGTCCG CTGGACATCG ACCTGCCGCA GTTAATCGTC     240

AAGGATACGC GTCTGGCGTT TGGTGAACTG GCTGCATGGG TTCGCCAGCA AGTTCCGGCG     300

CGCGTGGTTG CTCTGACGGG GTCCTCCGGC AAAACCTCCG TTAAAGAGAT GACGGCGGCG     360

ATTTTAAGCC AGTGCGGCAA CACGCTTTAT ACGGCAGGCA ATCTCAACAA CGACATCGGT     420

GTACCGATGA CGCTGTTGCG CTTAACGCCG GAATACGATT ACGCAGTTAT TGAACTTGGC     480

GCGAACCATC AGGGCGAAAT AGCCTGGACT GTGAGTCTGA CTCGCCCGGA ACGTGCGCTG     540

GTCAACAACC TGGCAGCGGC GCATCTGGAA GGTTTTGGCT CGCTTGCGGG TGTCGCGAAA     600

GCGAAAGGTG AAATCTTTAG CGGCCTGCCG GAAAACGGTA TCGCCATTAT GAACGCCGAC     660

AACAACGACT GGCTGAACTG GCAGAGCGTA ATTGGCTCAC GCAAAGTGTG GCGTTTCTCA     720

CCCAATGCCG CCAACAGCGA TTTCACCGCC ACCAATATCC ATGTCACCTC GCACGGTACG     780

GAATTTACCC TACAAACCCC AACCGGTAGC GTCGATGTTC TGCTGCCGTT GCCGGGGCGT     840

CACAATATTG CGAATGCGCT GACAGCCGCT GCGCTCTCCA TGTCCGTGGG CGCAACGCTT     900

GATGCTATCA AGCGGGGCT GGCAAATCTG AAAGCTGTTC CAGGCCGTCT GTTCCCCATC     960

CAACTGGCAG AAAACCAGTT GCTGCTCGAC GACTCCTACA ACGCCAATGT CGGTTCAATG    1020

ACTGCAGCAG TCCAGGTACT GGCTGAAATG CCGGGCTACC GCGTGCTGGT GGTGGGCGAT    1080

ATGGCGGAAC TGGGCGCTGA AAGCGAAGCC TGCCATGTAC AGGTGGGCGA GGCGGCAAAA    1140

GCTGCTGGTA TTGACCGCGT GTTAAGCGTG GGTAAACAAA GCCATGCTAT CAGCACCCGC    1200

CAGCGGCGTT GGCGAACATT TGCTGATAAA AACTGCGTTA ATTACGCGTC TTAAATTACT    1260

GATTGCTGAG CAACAGGTAA TTACGATTTT AGTTAAGGGT TCACGTAGTG CCGCCATGGA    1320

AGAGGTAGTA CGCGCTTTAC AGGAGAATGG GACATGTTAG                          1360
```

(2) INFORMATION FOR SEQ ID NO:2:

(i) SEQUENCE CHARACTERISTICS:
       (A) LENGTH: 4 amino acids
       (B) TYPE: amino acid
       (C) STRANDEDNESS: single

```
          (D) TOPOLOGY: linear (ix) FEATURE:
          (A) NAME/KEY: Modified-site
          (B) LOCATION: 2
          (D) OTHER INFORMATION: /note= "D-glutamic acid"

(ix) FEATURE:
          (A) NAME/KEY: Modified-site
          (B) LOCATION: 3
          (D) OTHER INFORMATION: /product= "Dpm"

(ix) FEATURE:
          (A) NAME/KEY: Modified-site
          (B) LOCATION: 4
          (D) OTHER INFORMATION: /note= "D-alanine"

(xi) SEQUENCE DESCRIPTION: SEQ ID NO:2:

Ala Xaa Xaa Xaa
1

(2) INFORMATION FOR SEQ ID NO:3:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ix) FEATURE:
          (A) NAME/KEY: prim_transcript
          (B) LOCATION: 1..30
          (D) OTHER INFORMATION: /note= "upstream primer designated
              gal-3"

(xi) SEQUENCE DESCRIPTION: SEQ ID NO:3:

GCTCTAGAGG CTAAATTCTT GTGTAAACGA                                        30

(2) INFORMATION FOR SEQ ID NO:4:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ix) FEATURE:
          (A) NAME/KEY: prim_transcript
          (B) LOCATION: 1..30
          (D) OTHER INFORMATION: /note= "downstream primer
              designated gal-4"

(xi) SEQUENCE DESCRIPTION: SEQ ID NO:4:

GCTCTAGATC TGCCAGCATT TCATAACCAA                                        30

(2) INFORMATION FOR SEQ ID NO:5:

(i) SEQUENCE CHARACTERISTICS:
          (A) LENGTH: 42 base pairs
          (B) TYPE: nucleic acid
          (C) STRANDEDNESS: single
          (D) TOPOLOGY: linear (ix) FEATURE:
          (A) NAME/KEY: prim_transcript
          (B) LOCATION: 1..42
          (D) OTHER INFORMATION: /note= "Upstream primer designated
              murF1"

(xi) SEQUENCE DESCRIPTION: SEQ ID NO:5:

CGAGCACTGC GAGAGATGAT TAGCGTAACC CTTAGCCAAC TT                          42
```

(2) INFORMATION FOR SEQ ID NO:6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ix) FEATURE:
        (A) NAME/KEY: prim_transcript
        (B) LOCATION: 1..31
        (D) OTHER INFORMATION: /note= "downstream primer
            designated murF2"

(xi) SEQUENCE DESCRIPTION: SEQ ID NO:6:

CAGCGCGTGC AGCAGGCTGA CAGTGGCGCG A                                 31

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ix) FEATURE:
        (A) NAME/KEY: prim_transcript
        (B) LOCATION: 1..28
        (D) OTHER INFORMATION: /note= "Upstream primer designated
            murE1"

(xi) SEQUENCE DESCRIPTION: SEQ ID NO:7:

GCCGGATCCG CGCCGGTCTT TGGTGCCA                                     28

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (A) NAME/KEY: prim_transcript
        (B) LOCATION: 1..27
        (D) OTHER INFORMATION: /note= "downstream primer
            designated murE2"

(xi) SEQUENCE DESCRIPTION: SEQ ID NO:8:

AAGGGATCCG CTAATCATGC AATCACC                                      27

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ix) FEATURE:
        (A) NAME/KEY: prim_transcript
        (B) LOCATION: 1..21
        (D) OTHER INFORMATION: /note= "downstream primer
            designated OrfY-1"

(xi) SEQUENCE DESCRIPTION: SEQ ID NO:9:

TAACGCCAGC GAACCTACAT C                                             21

(2) INFORMATION FOR SEQ ID NO:10:

(i) SEQUENCE CHARACTERISTICS:
        (A) LENGTH: 30 base pairs

```
            (B) TYPE: nucleic acid
            (C) STRANDEDNESS: single
            (D) TOPOLOGY: linear (ix) FEATURE:
            (A) NAME/KEY: prim_transcript
            (B) LOCATION: 1..30
            (D) OTHER INFORMATION: /note= "upstream primer designated
                murF3"

(xi) SEQUENCE DESCRIPTION: SEQ ID NO:10:

GCCGGATCCC GATCGCGTCA CGGTGGCGCG                                               30

(2) INFORMATION FOR SEQ ID NO:11:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ix) FEATURE:
            (A) NAME/KEY: prim_transcript
            (B) LOCATION: 1..39
            (D) OTHER INFORMATION: /note= "downstream primer
                designated murF4"

(xi) SEQUENCE DESCRIPTION: SEQ ID NO:11:

GAAGATCTCA GCGCGTGCAG CAGGCTGACA GTGGCGCGA                                     39
```